US010465217B2

(12) United States Patent
Kim et al.

(10) Patent No.: US 10,465,217 B2
(45) Date of Patent: Nov. 5, 2019

(54) MICROORGANISM PRODUCING O-ACETYL HOMOSERINE AND THE METHOD OF PRODUCING O-ACETYL HOMOSERINE USING THE SAME

(71) Applicant: CJ CHEILJEDANG CORPORATION, Seoul (KR)

(72) Inventors: Hyun Ah Kim, Seoul (KR); Ju Hee Seo, Gyeonggi-do (KR); Yong Uk Shin, Gyeonggi-do (KR); So Young Kim, Gyeonggi-do (KR); Sang Kyoum Kim, Gyeonggi-do (KR); Kwang Ho Na, Seoul (KR); Jee Yeon Bae, Seoul (KR); Sung Kwang Son, Seoul (KR); Hye Ryun Yoo, Seoul (KR); Jin Geun Choi, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 14/901,532

(22) PCT Filed: Jun. 22, 2015

(86) PCT No.: PCT/KR2015/006307
§ 371 (c)(1),
(2) Date: Dec. 28, 2015

(87) PCT Pub. No.: WO2015/199396
PCT Pub. Date: Dec. 30, 2015

(65) Prior Publication Data
US 2017/0101655 A1    Apr. 13, 2017

(30) Foreign Application Priority Data

Jun. 23, 2014 (KR) ........................ 10-2014-0076779

(51) Int. Cl.
| *C12N 1/21* | (2006.01) |
| *C12N 15/54* | (2006.01) |
| *C12N 15/53* | (2006.01) |
| *C12N 15/60* | (2006.01) |
| *C12N 9/10* | (2006.01) |
| *C12P 13/06* | (2006.01) |
| *C12N 9/12* | (2006.01) |
| *C12N 9/88* | (2006.01) |
| *C12N 15/52* | (2006.01) |

(52) U.S. Cl.
CPC ............ *C12P 13/06* (2013.01); *C12N 9/1029* (2013.01); *C12N 9/1205* (2013.01); *C12N 9/88* (2013.01); *C12N 15/52* (2013.01); *C12Y 203/01031* (2013.01); *C12Y 203/03001* (2013.01); *C12Y 207/01039* (2013.01); *C12Y 401/01031* (2013.01)

(58) Field of Classification Search
None
See application file for complete search history.

(56) References Cited

U.S. PATENT DOCUMENTS

| 8,465,952 | B2 | 6/2013 | Kim et al. | |
| 2008/0293101 | A1* | 11/2008 | Peters | C12N 9/0036 435/69.1 |
| 2011/0053253 | A1* | 3/2011 | Kim | C12N 9/0006 435/252.33 |
| 2012/0252077 | A1 | 10/2012 | Figge et al. | |
| 2012/0329105 | A1* | 12/2012 | Kuvaeva | C12N 9/0016 435/109 |
| 2013/0273615 | A1 | 10/2013 | Kim et al. | |

FOREIGN PATENT DOCUMENTS

| CN | 102002473 A | 4/2011 |
| CN | 103797027 A | 5/2014 |
| EP | 2 290 051 A1 | 3/2011 |
| EP | 2 657 250 A2 | 10/2013 |
| EP | 2 657 345 A1 | 10/2013 |
| JP | 58-170488 A | 10/1983 |
| JP | 2011-45360 A | 3/2011 |
| KR | 10-0905381 B1 | 6/2009 |
| KR | 10-0951766 B1 | 4/2010 |
| KR | 10-2011-0023703 A | 3/2011 |
| KR | 10-1117012 B1 | 3/2012 |
| KR | 10-2012-0070531 A | 6/2012 |
| WO | 2008/013432 A1 | 1/2008 |
| WO | 2010/038905 A1 | 4/2010 |
| WO | 2011/073738 A1 | 6/2011 |
| WO | 2012/087039 A1 | 6/2012 |

OTHER PUBLICATIONS

Viola, The Central Enzymes of the Aspartate Family of Amino Acid Biosynthesis, Acc. Chem. Res., 2001, 34, 339-49.*
Zubieta et al., A Single Amino Acid Change Is Responsible for Evolution of Acyltransferase Specificity in Bacterial Methionine Biosynthesis, J. Biol. Chem., 2008, 283, 7561-67.*
Soma et al., Metabolic flux redirection from a central metabolic pathway toward a synthetic pathway using a metabolic toggle switch, Metabolic Eng., Feb. 2014, 23, 175-84.*
Datsenko et al., "One-step inactivation of chromosomal genes in *Escherichia coli* K-12 using PCR products," PNAS 97(12): 6640-6645, Jun. 6, 2000.
Nakashima et al., "Multiple-Gene Silencing Using Antisense RNAs in *Escherichia coli*," Michael Kaufmann and Claudia Klinger (eds.), Functional Genomics: Methods and Protocols, Methods in Molecular Biology 815: 307-319, 2012.
Soma et al., "Metabolic flux redirection from a central metabolic pathway toward a synthetic pathway using a metabolic toggle switch," Metabolic Engineering 23: 175-184, May 2014.

(Continued)

*Primary Examiner* — Robert B Mondesi
*Assistant Examiner* — Todd M Epstein
(74) *Attorney, Agent, or Firm* — Cooley LLP

(57) ABSTRACT

Disclosed is a microorganism of *Escherichia* sp. producing O-acetyl homoserine, and a method of producing O-acetyl homoserine in high yield using the microorganism.

6 Claims, 2 Drawing Sheets

Specification includes a Sequence Listing.

(56) References Cited

OTHER PUBLICATIONS

Stokell et al., "Probing the Roles of Key Residues in the Unique Regulatory NADH Binding Site of Type II Citrate Synthase of *Escherichia coli*," The Journal of Biological Chemistry 278 (37): 35435-35443, 2003.
Vandedrinck et al., "Metabolic engineering of *Escherichia coli*: construction and characterization of a gltA (citrate synthase) knock-out mutant," Meded Rijksuniv Gent Fak Landbouwkd Toegep Biol Wet. 66(3a):333-6, 2001 (PubMed abstract only).
Harford et al, "Evidence for Isosteric and Allosteric Nucleotide Inhibition of Citrate Synthase from Multiple-Inhibition Studies", Biochem. J. (1975) 151, 455-458.
Pereira et al, "Tee Active Site Mutants of *Escherichia coli* Citrate Synthase Effects of Mutations on Catalytic and Allosteric Properties* (Received for publication, May 17, 1993)", Jan. 7, 1994 (Jan. 7, 1994), pp. 412-417, Retrieved from the Internet: URL: http:www.jbc.org/content/269/1/412.full.pdf.
Kim et al., "Proteomic Response Analysis of a Threonine-Overproducing Mutant of *Escherichia coli*," Biochem J, 381(3):823-829 (2004).

* cited by examiner

[FIG. 1]
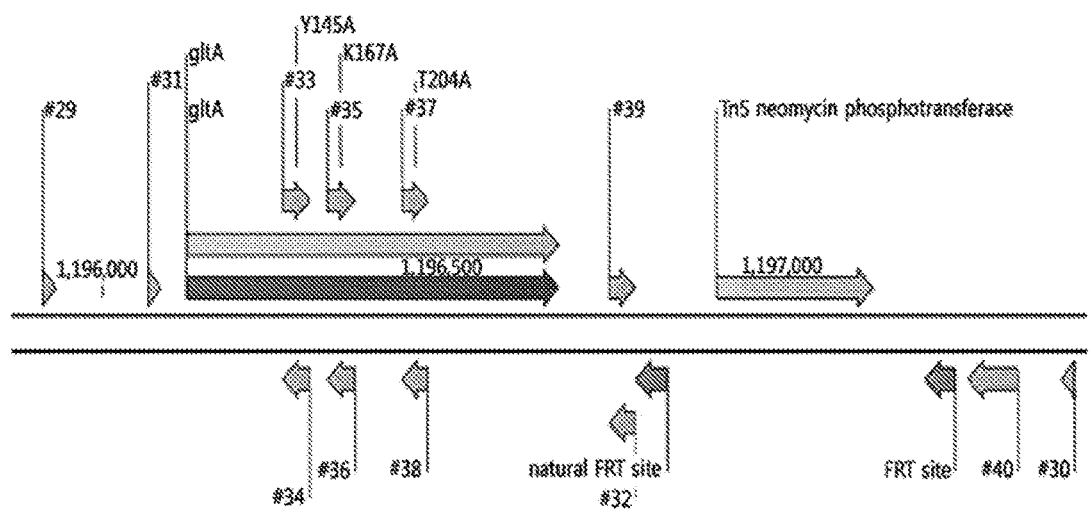

[FIG. 2]
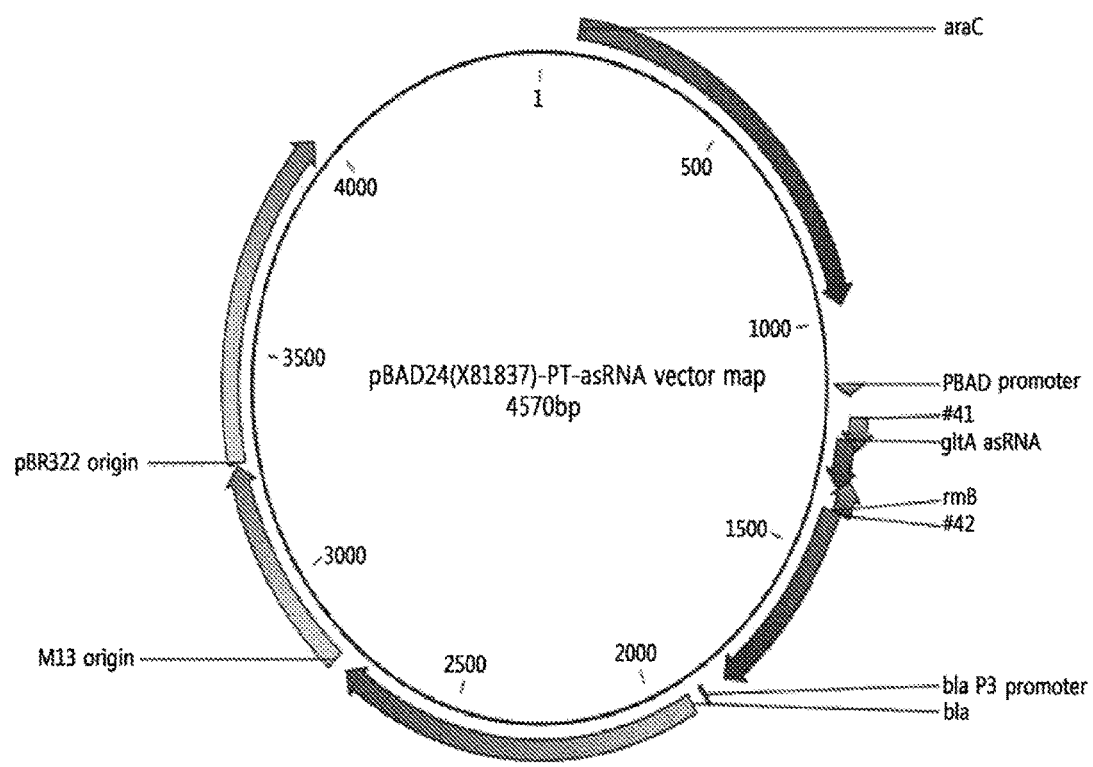

SEQUENCE LISTING

<160> NUMBER OF SEQ ID NOS: 71

<210> SEQ ID NO 1
<211> LENGTH: 427
<212> TYPE: PRT
<213> ORGANISM: Artificial Sequence
<220> FEATURE:
<223> OTHER INFORMATION: GltA A145

<400> SEQUENCE: 1

Met Ala Asp Thr Lys Ala Lys Leu Thr Leu Asn Gly Asp Thr Ala Val
1               5                   10                  15

Glu Leu Asp Val Leu Lys Gly Thr Leu Gly Gln Asp Val Ile Asp Ile
                20                  25                  30

Arg Thr Leu Gly Ser Lys Gly Val Phe Thr Phe Asp Pro Gly Phe Thr
            35                  40                  45

Ser Thr Ala Ser Cys Glu Ser Lys Ile Thr Phe Ile Asp Gly Asp Glu
    50                  55                  60

Gly Ile Leu Leu His Arg Gly Phe Pro Ile Asp Gln Leu Ala Thr Asp
65                  70                  75                  80

Ser Asn Tyr Leu Glu Val Cys Tyr Ile Leu Leu Asn Gly Glu Lys Pro
                85                  90                  95

Thr Gln Glu Gln Tyr Asp Glu Phe Lys Thr Thr Val Thr Arg His Thr
            100                 105                 110

Met Ile His Glu Gln Ile Thr Arg Leu Phe His Ala Phe Arg Arg Asp
        115                 120                 125

Ser His Pro Met Ala Val Met Cys Gly Ile Thr Gly Ala Leu Ala Ala
    130                 135                 140

Phe Ala His Asp Ser Leu Asp Val Asn Asn Pro Arg His Arg Glu Ile
145                 150                 155                 160

Ala Ala Phe Arg Leu Leu Ser Lys Met Pro Thr Met Ala Ala Met Cys
                165                 170                 175

Tyr Lys Tyr Ser Ile Gly Gln Pro Phe Val Tyr Pro Arg Asn Asp Leu
            180                 185                 190

Ser Tyr Ala Gly Asn Phe Leu Asn Met Met Phe Ser Thr Pro Cys Glu
        195                 200                 205

Pro Tyr Glu Val Asn Pro Ile Leu Glu Arg Ala Met Asp Arg Ile Leu
    210                 215                 220

Ile Leu His Ala Asp His Glu Gln Asn Ala Ser Thr Ser Thr Val Arg
225                 230                 235                 240

Thr Ala Gly Ser Ser Gly Ala Asn Pro Phe Ala Cys Ile Ala Ala Gly
                245                 250                 255

Ile Ala Ser Leu Trp Gly Pro Ala His Gly Gly Ala Asn Glu Ala Ala
            260                 265                 270

Leu Lys Met Leu Glu Glu Ile Ser Ser Val Lys His Ile Pro Glu Phe
        275                 280                 285

Val Arg Arg Ala Lys Asp Lys Asn Asp Ser Phe Arg Leu Met Gly Phe
    290                 295                 300

Gly His Arg Val Tyr Lys Asn Tyr Asp Pro Arg Ala Thr Val Met Arg
305                 310                 315                 320

Glu Thr Cys His Glu Val Leu Lys Glu Leu Gly Thr Lys Asp Asp Leu
                325                 330                 335

Leu Glu Val Ala Met Glu Leu Glu Asn Ile Ala Leu Asn Asp Pro Tyr
            340                 345                 350

Phe Ile Glu Lys Lys Leu Tyr Pro Asn Val Asp Phe Tyr Ser Gly Ile

```
                355                 360                 365
Ile Leu Lys Ala Met Gly Ile Pro Ser Ser Met Phe Thr Val Ile Phe
370                 375                 380

Ala Met Ala Arg Thr Val Gly Trp Ile Ala His Trp Ser Glu Met His
385                 390                 395                 400

Ser Asp Gly Met Lys Ile Ala Arg Pro Arg Gln Leu Tyr Thr Gly Tyr
                405                 410                 415

Glu Lys Arg Asp Phe Lys Ser Asp Ile Lys Arg
            420                 425

<210> SEQ ID NO 2
<211> LENGTH: 427
<212> TYPE: PRT
<213> ORGANISM: Artificial Sequence
<220> FEATURE:
<223> OTHER INFORMATION: GltA A167

<400> SEQUENCE: 2

Met Ala Asp Thr Lys Ala Lys Leu Thr Leu Asn Gly Asp Thr Ala Val
1               5                   10                  15

Glu Leu Asp Val Leu Lys Gly Thr Leu Gly Gln Asp Val Ile Asp Ile
                20                  25                  30

Arg Thr Leu Gly Ser Lys Gly Val Phe Thr Phe Asp Pro Gly Phe Thr
            35                  40                  45

Ser Thr Ala Ser Cys Glu Ser Lys Ile Thr Phe Ile Asp Gly Asp Glu
        50                  55                  60

Gly Ile Leu Leu His Arg Gly Phe Pro Ile Asp Gln Leu Ala Thr Asp
65                  70                  75                  80

Ser Asn Tyr Leu Glu Val Cys Tyr Ile Leu Leu Asn Gly Glu Lys Pro
                85                  90                  95

Thr Gln Glu Gln Tyr Asp Glu Phe Lys Thr Thr Val Thr Arg His Thr
            100                 105                 110

Met Ile His Glu Gln Ile Thr Arg Leu Phe His Ala Phe Arg Arg Asp
        115                 120                 125

Ser His Pro Met Ala Val Met Cys Gly Ile Thr Gly Ala Leu Ala Ala
130                 135                 140

Phe Tyr His Asp Ser Leu Asp Val Asn Asn Pro Arg His Arg Glu Ile
145                 150                 155                 160

Ala Ala Phe Arg Leu Leu Ser Ala Met Pro Thr Met Ala Ala Met Cys
                165                 170                 175

Tyr Lys Tyr Ser Ile Gly Gln Pro Phe Val Tyr Pro Arg Asn Asp Leu
            180                 185                 190

Ser Tyr Ala Gly Asn Phe Leu Asn Met Met Phe Ser Thr Pro Cys Glu
        195                 200                 205

Pro Tyr Glu Val Asn Pro Ile Leu Glu Arg Ala Met Asp Arg Ile Leu
210                 215                 220

Ile Leu His Ala Asp His Glu Gln Asn Ala Ser Thr Ser Thr Val Arg
225                 230                 235                 240

Thr Ala Gly Ser Ser Gly Ala Asn Pro Phe Ala Cys Ile Ala Ala Gly
                245                 250                 255

Ile Ala Ser Leu Trp Gly Pro Ala His Gly Gly Ala Asn Glu Ala Ala
            260                 265                 270

Leu Lys Met Leu Glu Glu Ile Ser Ser Val Lys His Ile Pro Glu Phe
        275                 280                 285

Val Arg Arg Ala Lys Asp Lys Asn Asp Ser Phe Arg Leu Met Gly Phe
```

```
            290                 295                 300
Gly His Arg Val Tyr Lys Asn Tyr Asp Pro Arg Ala Thr Val Met Arg
305                 310                 315                 320

Glu Thr Cys His Glu Val Leu Lys Glu Leu Gly Thr Lys Asp Asp Leu
                325                 330                 335

Leu Glu Val Ala Met Glu Leu Glu Asn Ile Ala Leu Asn Asp Pro Tyr
                340                 345                 350

Phe Ile Glu Lys Lys Leu Tyr Pro Asn Val Asp Phe Tyr Ser Gly Ile
                355                 360                 365

Ile Leu Lys Ala Met Gly Ile Pro Ser Ser Met Phe Thr Val Ile Phe
370                 375                 380

Ala Met Ala Arg Thr Val Gly Trp Ile Ala His Trp Ser Glu Met His
385                 390                 395                 400

Ser Asp Gly Met Lys Ile Ala Arg Pro Arg Gln Leu Tyr Thr Gly Tyr
                405                 410                 415

Glu Lys Arg Asp Phe Lys Ser Asp Ile Lys Arg
                420                 425
```

<210> SEQ ID NO 3
<211> LENGTH: 427
<212> TYPE: PRT
<213> ORGANISM: Artificial Sequence
<220> FEATURE:
<223> OTHER INFORMATION: GltA A204

<400> SEQUENCE: 3

```
Met Ala Asp Thr Lys Ala Lys Leu Thr Leu Asn Gly Asp Thr Ala Val
1               5                   10                  15

Glu Leu Asp Val Leu Lys Gly Thr Leu Gly Gln Asp Val Ile Asp Ile
                20                  25                  30

Arg Thr Leu Gly Ser Lys Gly Val Phe Thr Phe Asp Pro Gly Phe Thr
            35                  40                  45

Ser Thr Ala Ser Cys Glu Ser Lys Ile Thr Phe Ile Asp Gly Asp Glu
        50                  55                  60

Gly Ile Leu Leu His Arg Gly Phe Pro Ile Asp Gln Leu Ala Thr Asp
65                  70                  75                  80

Ser Asn Tyr Leu Glu Val Cys Tyr Ile Leu Leu Asn Gly Glu Lys Pro
                85                  90                  95

Thr Gln Glu Gln Tyr Asp Glu Phe Lys Thr Thr Val Thr Arg His Thr
                100                 105                 110

Met Ile His Glu Gln Ile Thr Arg Leu Phe His Ala Phe Arg Arg Asp
            115                 120                 125

Ser His Pro Met Ala Val Met Cys Gly Ile Thr Gly Ala Leu Ala Ala
        130                 135                 140

Phe Tyr His Asp Ser Leu Asp Val Asn Asn Pro Arg His Arg Glu Ile
145                 150                 155                 160

Ala Ala Phe Arg Leu Leu Ser Lys Met Pro Thr Met Ala Ala Met Cys
                165                 170                 175

Tyr Lys Tyr Ser Ile Gly Gln Pro Phe Val Tyr Pro Arg Asn Asp Leu
                180                 185                 190

Ser Tyr Ala Gly Asn Phe Leu Asn Met Met Phe Ser Ala Pro Cys Glu
            195                 200                 205

Pro Tyr Glu Val Asn Pro Ile Leu Glu Arg Ala Met Asp Arg Ile Leu
        210                 215                 220

Ile Leu His Ala Asp His Glu Gln Asn Ala Ser Thr Ser Thr Val Arg
```

```
                225                 230                 235                 240
        Thr Ala Gly Ser Ser Gly Ala Asn Pro Phe Ala Cys Ile Ala Ala Gly
                        245                 250                 255

Ile Ala Ser Leu Trp Gly Pro Ala His Gly Ala Asn Glu Ala Ala
                        260                 265                 270

Leu Lys Met Leu Glu Glu Ile Ser Ser Val Lys His Ile Pro Glu Phe
                        275                 280                 285

Val Arg Arg Ala Lys Asp Lys Asn Asp Ser Phe Arg Leu Met Gly Phe
                        290                 295                 300

Gly His Arg Val Tyr Lys Asn Tyr Asp Pro Arg Ala Thr Val Met Arg
        305                 310                 315                 320

Glu Thr Cys His Glu Val Leu Lys Glu Leu Gly Thr Lys Asp Asp Leu
                        325                 330                 335

Leu Glu Val Ala Met Glu Leu Glu Asn Ile Ala Leu Asn Asp Pro Tyr
                        340                 345                 350

Phe Ile Glu Lys Lys Leu Tyr Pro Asn Val Asp Phe Tyr Ser Gly Ile
                        355                 360                 365

Ile Leu Lys Ala Met Gly Ile Pro Ser Ser Met Phe Thr Val Ile Phe
                        370                 375                 380

Ala Met Ala Arg Thr Val Gly Trp Ile Ala His Trp Ser Glu Met His
        385                 390                 395                 400

Ser Asp Gly Met Lys Ile Ala Arg Pro Arg Gln Leu Tyr Thr Gly Tyr
                        405                 410                 415

Glu Lys Arg Asp Phe Lys Ser Asp Ile Lys Arg
                        420                 425

<210> SEQ ID NO 4
<211> LENGTH: 427
<212> TYPE: PRT
<213> ORGANISM: Escherichia coli
<220> FEATURE:
<221> NAME/KEY: PEPTIDE
<222> LOCATION: (1)..(427)
<223> OTHER INFORMATION: GltA

<400> SEQUENCE: 4

Met Ala Asp Thr Lys Ala Lys Leu Thr Leu Asn Gly Asp Thr Ala Val
1               5                   10                  15

Glu Leu Asp Val Leu Lys Gly Thr Leu Gly Gln Asp Val Ile Asp Ile
                20                  25                  30

Arg Thr Leu Gly Ser Lys Gly Val Phe Thr Phe Asp Pro Gly Phe Thr
            35                  40                  45

Ser Thr Ala Ser Cys Glu Ser Lys Ile Thr Phe Ile Asp Gly Asp Glu
        50                  55                  60

Gly Ile Leu Leu His Arg Gly Phe Pro Ile Asp Gln Leu Ala Thr Asp
65                  70                  75                  80

Ser Asn Tyr Leu Glu Val Cys Tyr Ile Leu Leu Asn Gly Glu Lys Pro
                85                  90                  95

Thr Gln Glu Gln Tyr Asp Glu Phe Lys Thr Thr Val Thr Arg His Thr
            100                 105                 110

Met Ile His Glu Gln Ile Thr Arg Leu Phe His Ala Phe Arg Arg Asp
        115                 120                 125

Ser His Pro Met Ala Val Met Cys Gly Ile Thr Gly Ala Leu Ala Ala
    130                 135                 140

Phe Tyr His Asp Ser Leu Asp Val Asn Asn Pro Arg His Arg Glu Ile
145                 150                 155                 160
```

```
Ala Ala Phe Arg Leu Leu Ser Lys Met Pro Thr Met Ala Ala Met Cys
            165                 170                 175

Tyr Lys Tyr Ser Ile Gly Gln Pro Phe Val Tyr Pro Arg Asn Asp Leu
            180                 185                 190

Ser Tyr Ala Gly Asn Phe Leu Asn Met Met Phe Ser Thr Pro Cys Glu
            195                 200                 205

Pro Tyr Glu Val Asn Pro Ile Leu Glu Arg Ala Met Asp Arg Ile Leu
            210                 215                 220

Ile Leu His Ala Asp His Glu Gln Asn Ala Ser Thr Ser Thr Val Arg
225                 230                 235                 240

Thr Ala Gly Ser Ser Gly Ala Asn Pro Phe Ala Cys Ile Ala Ala Gly
            245                 250                 255

Ile Ala Ser Leu Trp Gly Pro Ala His Gly Gly Ala Asn Glu Ala Ala
            260                 265                 270

Leu Lys Met Leu Glu Glu Ile Ser Ser Val Lys His Ile Pro Glu Phe
            275                 280                 285

Val Arg Arg Ala Lys Asp Lys Asn Asp Ser Phe Arg Leu Met Gly Phe
            290                 295                 300

Gly His Arg Val Tyr Lys Asn Tyr Asp Pro Arg Ala Thr Val Met Arg
305                 310                 315                 320

Glu Thr Cys His Glu Val Leu Lys Glu Leu Gly Thr Lys Asp Asp Leu
            325                 330                 335

Leu Glu Val Ala Met Glu Leu Glu Asn Ile Ala Leu Asn Asp Pro Tyr
            340                 345                 350

Phe Ile Glu Lys Lys Leu Tyr Pro Asn Val Asp Phe Tyr Ser Gly Ile
            355                 360                 365

Ile Leu Lys Ala Met Gly Ile Pro Ser Ser Met Phe Thr Val Ile Phe
            370                 375                 380

Ala Met Ala Arg Thr Val Gly Trp Ile Ala His Trp Ser Glu Met His
385                 390                 395                 400

Ser Asp Gly Met Lys Ile Ala Arg Pro Arg Gln Leu Tyr Thr Gly Tyr
            405                 410                 415

Glu Lys Arg Asp Phe Lys Ser Asp Ile Lys Arg
            420                 425

<210> SEQ ID NO 5
<211> LENGTH: 1284
<212> TYPE: DNA
<213> ORGANISM: Artificial Sequence
<220> FEATURE:
<223> OTHER INFORMATION: GltA A145

<400> SEQUENCE: 5
atggctgata caaaagcaaa actcaccctc aacggggata cagctgttga actggatgtg      60
ctgaaaggca cgctgggtca agatgttatt gatatccgta ctctcggttc aaaaggtgtg     120
ttcacctttg acccaggctt cacttcaacc gcatcctgcg aatctaaaat tactttttatt    180 gatggtgatg aaggtatttt gctgcaccgc ggtttcccga tcgatcagct ggcgaccgat     240
tctaactacc tggaagtttg ttacatcctg ctgaatggtg aaaaaccgac tcaggaacag     300
tatgacgaat ttaaaactac ggtgacccgt cataccatga tccacgagca gattacccgt     360
ctgttccatg ctttccgtcg cgactcgcat ccaatggcag tcatgtgtgg tattaccggc     420
gcgctggcgg cgttcgcgca cgactcgctg atgttaaca atcctcgtca ccgtgaaatt      480
gccgcgttcc gcctgctgtc gaaaatgccg accatggccg cgatgtgtta caagtattcc     540
```

```
attggtcagc catttgttta cccgcgcaac gatctctcct acgccggtaa cttcctgaat    600
atgatgttct ccacgccgtg cgaaccgtat gaagttaatc cgattctgga acgtgctatg    660
gaccgtattc tgatcctgca cgctgaccat gaacagaacg cctctacctc caccgtgcgt    720
accgctggct cttcgggtgc gaacccgttt gcctgtatcg cagcaggtat tgcttcactg    780
tggggacctg cgcacggcgg tgctaacgaa gcggcgctga aaatgctgga agaaatcagc    840
tccgttaaac acattccgga atttgttcgt cgtgcgaaag acaaaaatga ttctttccgc    900
ctgatgggct tcggtcaccg cgtgtacaaa aattacgacc gcgcgccac cgtaatgcgt     960
gaaacctgcc atgaagtgct gaaagagctg ggcacgaagg atgacctgct ggaagtggct   1020
atggagctgg aaaacatcgc gctgaacgac ccgtacttta tcgagaagaa actgtacccg   1080
aacgtcgatt tctactctgg tatcatcctg aaagcgatgg gtattccgtc ttccatgttc   1140
accgtcattt tcgcaatggc acgtaccgtt ggctggatcg cccactggag cgaaatgcac   1200
agtgacggta tgaagattgc ccgtccgcgt cagctgtata caggatatga aaaacgcgac   1260
tttaaaagcg atatcaagcg ttaa                                          1284

<210> SEQ ID NO 6
<211> LENGTH: 1284
<212> TYPE: DNA
<213> ORGANISM: Artificial Sequence
<220> FEATURE:
<223> OTHER INFORMATION: GltA A167

<400> SEQUENCE: 6
atggctgata caaaagcaaa actcaccctc aacggggata cagctgttga actggatgtg     60
ctgaaaggca cgctgggtca agatgttatt gatatccgta ctctcggttc aaaaggtgtg    120
ttcacctttg acccaggctt cacttcaacc gcatcctgcg aatctaaaat tacttttatt    180
gatggtgatg aagtatttt gctgcaccgc ggtttcccga tcgatcagct ggcgaccgat    240
tctaactacc tggaagtttg ttacatcctg ctgaatggta aaaaaccgac tcaggaacag    300
tatgacgaat ttaaaactac ggtgacccgt cataccatga tccacgagca gattacccgt    360
ctgttccatg ctttccgtcg cgactcgcat ccaatggcag tcatgtgtgg tattaccggc    420
gcgctggcgg cgttctatca cgactcgctg atgttaaca atcctcgtca ccgtgaaatt    480
gccgcgttcc gcctgctgtc ggcgatgccg accatggccg cgatgtgtta caagtattcc    540
attggtcagc catttgttta cccgcgcaac gatctctcct acgccggtaa cttcctgaat    600
atgatgttct ccacgccgtg cgaaccgtat gaagttaatc cgattctgga acgtgctatg    660
gaccgtattc tgatcctgca cgctgaccat gaacagaacg cctctacctc caccgtgcgt    720
accgctggct cttcgggtgc gaacccgttt gcctgtatcg cagcaggtat tgcttcactg    780
tggggacctg cgcacggcgg tgctaacgaa gcggcgctga aaatgctgga agaaatcagc    840
tccgttaaac acattccgga atttgttcgt cgtgcgaaag acaaaaatga ttctttccgc    900
ctgatgggct tcggtcaccg cgtgtacaaa aattacgacc gcgcgccac cgtaatgcgt     960
gaaacctgcc atgaagtgct gaaagagctg ggcacgaagg atgacctgct ggaagtggct   1020
atggagctgg aaaacatcgc gctgaacgac ccgtacttta tcgagaagaa actgtacccg   1080
aacgtcgatt tctactctgg tatcatcctg aaagcgatgg gtattccgtc ttccatgttc   1140
accgtcattt tcgcaatggc acgtaccgtt ggctggatcg cccactggag cgaaatgcac   1200
agtgacggta tgaagattgc ccgtccgcgt cagctgtata caggatatga aaaacgcgac   1260
```
tttaaaagcg atatcaagcg ttaa                                            1284

<210> SEQ ID NO 7
<211> LENGTH: 1284
<212> TYPE: DNA
<213> ORGANISM: Artificial Sequence
<220> FEATURE:
<223> OTHER INFORMATION: GltA A204

<400> SEQUENCE: 7

| | | |
|---|---|---|
| atggctgata caaaagcaaa actcaccctc aacggggata cagctgttga actggatgtg | 60 |
| ctgaaaggca cgctgggtca agatgttatt gatatccgta ctctcggttc aaaaggtgtg | 120 |
| ttcacctttg acccaggctt cacttcaacc gcatcctgcg aatctaaaat tacttttatt | 180 |
| gatggtgatg aaggtatttt gctgcaccgc ggtttcccga tcgatcagct ggcgaccgat | 240 |
| tctaactacc tggaagtttg ttacatcctg ctgaatggtg aaaaaccgac tcaggaacag | 300 |
| tatgacgaat ttaaaactac ggtgacccgt cataccatga tccacgagca gattacccgt | 360 |
| ctgttccatg ctttccgtcg cgactcgcat ccaatggcag tcatgtgtgg tattaccggc | 420 |
| gcgctggcgg cgttctatca cgactcgctg atgttaaca atcctcgtca ccgtgaaatt | 480 |
| gccgcgttcc gcctgctgtc gaaaatgccg accatggccg cgatgtgtta caagtattcc | 540 |
| attggtcagc catttgttta cccgcgcaac gatctctcct acgccggtaa cttcctgaat | 600 |
| atgatgttct ccgcgccgtg cgaaccgtat gaagttaatc cgattctgga acgtgctatg | 660 |
| gaccgtattc tgatcctgca cgctgaccat gaacagaacg cctctacctc caccgtgcgt | 720 |
| accgctggct cttcgggtgc gaacccgttt gcctgtatcg cagcaggtat tgcttcactg | 780 |
| tggggacctg cgcacggcgg tgctaacgaa gcggcgctga aaatgctgga agaaatcagc | 840 |
| tccgttaaac acattccgga atttgttcgt cgtgcgaaag acaaaaatga ttctttccgc | 900 |
| ctgatgggct tcggtcaccg cgtgtacaaa aattacgacc cgcgcgccac cgtaatgcgt | 960 |
| gaaacctgcc atgaagtgct gaagagctg ggcacgaagg atgacctgct ggaagtggct | 1020 |
| atggagctgg aaaacatcgc gctgaacgac ccgtacttta tcgagaagaa actgtacccg | 1080 |
| aacgtcgatt tctactctgg tatcatcctg aaagcgatgg gtattccgtc ttccatgttc | 1140 |
| accgtcattt tcgcaatggc acgtaccgtt ggctggatcg cccactggag cgaaatgcac | 1200 |
| agtgacggta tgaagattgc ccgtccgcgt cagctgtata caggatatga aaaacgcgac | 1260 |
| tttaaaagcg atatcaagcg ttaa | 1284 |

<210> SEQ ID NO 8
<211> LENGTH: 1284
<212> TYPE: DNA
<213> ORGANISM: Escherichia coli
<220> FEATURE:
<221> NAME/KEY: gene
<222> LOCATION: (1)..(1284)
<223> OTHER INFORMATION: GltA

<400> SEQUENCE: 8

| | | |
|---|---|---|
| atggctgata caaaagcaaa actcaccctc aacggggata cagctgttga actggatgtg | 60 |
| ctgaaaggca cgctgggtca agatgttatt gatatccgta ctctcggttc aaaaggtgtg | 120 |
| ttcacctttg acccaggctt cacttcaacc gcatcctgcg aatctaaaat tacttttatt | 180 |
| gatggtgatg aaggtatttt gctgcaccgc ggtttcccga tcgatcagct ggcgaccgat | 240 |
| tctaactacc tggaagtttg ttacatcctg ctgaatggtg aaaaaccgac tcaggaacag | 300 |
| tatgacgaat ttaaaactac ggtgacccgt cataccatga tccacgagca gattacccgt | 360 |

```
ctgttccatg ctttccgtcg cgactcgcat ccaatggcag tcatgtgtgg tattaccggc    420
gcgctggcgg cgttctatca cgactcgctg gatgttaaca atcctcgtca ccgtgaaatt    480
gccgcgttcc gcctgctgtc gaaaatgccg accatggccg cgatgtgtta caagtattcc    540
attggtcagc catttgttta cccgcgcaac gatctctcct acgccggtaa cttcctgaat    600
atgatgttct ccacgccgtg cgaaccgtat gaagttaatc cgattctgga acgtgctatg    660
gaccgtattc tgatcctgca cgctgaccat gaacagaacg cctctacctc caccgtgcgt    720
accgctggct cttcgggtgc gaacccgttt gcctgtatcg cagcaggtat tgcttcactg    780
tggggacctg cgcacggcgg tgctaacgaa gcggcgctga aaatgctgga gaaaatcagc    840
tccgttaaac acattccgga atttgttcgt cgtgcgaaag acaaaaatga ttctttccgc    900
ctgatgggct tcggtcaccg cgtgtacaaa aattacgacc cgcgcgccac cgtaatgcgt    960
gaaacctgcc atgaagtgct gaaagagctg ggcacgaagg atgacctgct ggaagtggct   1020
atggagctgg aaaacatcgc gctgaacgac ccgtacttta tcgagaagaa actgtacccg   1080
aacgtcgatt tctactctgg tatcatcctg aaagcgatgg gtattccgtc ttccatgttc   1140
accgtcattt tcgcaatggc acgtaccgtt ggctggatcg cccactggag cgaaatgcac   1200
agtgacggta tgaagattgc ccgtccgcgt cagctgtata caggatatga aaaacgcgac   1260
tttaaaagcg atatcaagcg ttaa                                          1284

<210> SEQ ID NO 9
<211> LENGTH: 386
<212> TYPE: PRT
<213> ORGANISM: Escherichia coli
<220> FEATURE:
<221> NAME/KEY: PEPTIDE
<222> LOCATION: (1)..(386)
<223> OTHER INFORMATION: metB

<400> SEQUENCE: 9

Met Thr Arg Lys Gln Ala Thr Ile Ala Val Arg Ser Gly Leu Asn Asp
1               5                   10                  15

Asp Glu Gln Tyr Gly Cys Val Val Pro Pro Ile His Leu Ser Ser Thr
            20                  25                  30

Tyr Asn Phe Thr Gly Phe Asn Glu Pro Arg Ala His Asp Tyr Ser Arg
        35                  40                  45

Arg Gly Asn Pro Thr Arg Asp Val Val Gln Arg Ala Leu Ala Glu Leu
    50                  55                  60

Glu Gly Gly Ala Gly Ala Val Leu Thr Asn Thr Gly Met Ser Ala Ile
65                  70                  75                  80

His Leu Val Thr Thr Val Phe Leu Lys Pro Gly Asp Leu Leu Val Ala
                85                  90                  95

Pro His Asp Cys Tyr Gly Gly Ser Tyr Arg Leu Phe Asp Ser Leu Ala
            100                 105                 110

Lys Arg Gly Cys Tyr Arg Val Leu Phe Val Asp Gln Gly Asp Glu Gln
        115                 120                 125

Ala Leu Arg Ala Ala Leu Ala Glu Lys Pro Lys Leu Val Leu Val Glu
    130                 135                 140

Ser Pro Ser Asn Pro Leu Leu Arg Val Val Asp Ile Ala Lys Ile Cys
145                 150                 155                 160

His Leu Ala Arg Glu Val Gly Ala Val Ser Val Val Asp Asn Thr Phe
                165                 170                 175

Leu Ser Pro Ala Leu Gln Asn Pro Leu Ala Leu Gly Ala Asp Leu Val
```

```
                180                 185                 190
Leu His Ser Cys Thr Lys Tyr Leu Asn Gly His Ser Asp Val Val Ala
            195                 200                 205
Gly Val Val Ile Ala Lys Asp Pro Asp Val Val Thr Glu Leu Ala Trp
            210                 215                 220
Trp Ala Asn Asn Ile Gly Val Thr Gly Gly Ala Phe Asp Ser Tyr Leu
225                 230                 235                 240
Leu Leu Arg Gly Leu Arg Thr Leu Val Pro Arg Met Glu Leu Ala Gln
            245                 250                 255
Arg Asn Ala Gln Ala Ile Val Lys Tyr Leu Gln Thr Gln Pro Leu Val
            260                 265                 270
Lys Lys Leu Tyr His Pro Ser Leu Pro Glu Asn Gln Gly His Glu Ile
            275                 280                 285
Ala Ala Arg Gln Gln Lys Gly Phe Gly Ala Met Leu Ser Phe Glu Leu
            290                 295                 300
Asp Gly Asp Glu Gln Thr Leu Arg Arg Phe Leu Gly Gly Leu Ser Leu
305                 310                 315                 320
Phe Thr Leu Ala Glu Ser Leu Gly Gly Val Glu Ser Leu Ile Ser His
            325                 330                 335
Ala Ala Thr Met Thr His Ala Gly Met Ala Pro Glu Ala Arg Ala Ala
            340                 345                 350
Ala Gly Ile Ser Glu Thr Leu Leu Arg Ile Ser Thr Gly Ile Glu Asp
            355                 360                 365
Gly Glu Asp Leu Ile Ala Asp Leu Glu Asn Gly Phe Arg Ala Ala Asn
            370                 375                 380
Lys Gly
385

<210> SEQ ID NO 10
<211> LENGTH: 1161
<212> TYPE: DNA
<213> ORGANISM: Escherichia coli
<220> FEATURE:
<221> NAME/KEY: gene
<222> LOCATION: (1)..(1161)
<223> OTHER INFORMATION: metB

<400> SEQUENCE: 10
atgacgcgta acaggccac  catcgcagtg cgtagcgggt aaatgacga  cgaacagtat      60 ggttgcgttg tcccaccgat ccatctttcc agcacctata actttaccgg atttaatgaa     120
ccgcgcgcgc atgattactc gcgtcgcggc aacccaacgc gcgatgtggt tcagcgtgcg     180
ctggcagaac tggaaggtgg tgctggtgca gtacttacta taccggcat  gtccgcgatt     240 cacctggtaa cgaccgtctt tttgaaacct ggcgatctgc tggttgcgcc gcacgactgc     300
tacggcggta gctatcgcct gttcgacagt ctggcgaaac gcggttgcta tcgcgtgttg     360
tttgttgatc aaggcgatga acaggcatta cgggcagcgc tggcagaaaa acccaaactg     420
gtactggtag aaagcccaag taatccattg ttacgcgtcg tggatattgc gaaaatctgc     480
catctggcaa gggaagtcgg ggcggtgagc gtggtggata caccttcttc aagcccggca     540
ttacaaaatc cgctggcatt aggtgccgat ctggtgttgc attcatgcac gaaatatctg     600
aacggtcact cagacgtagt ggccggcgtg gtgattgcta agacccgga  cgttgtcact     660 gaactggcct ggtgggcaaa caatattggc gtgacgggcg gcgcgtttga cagctatctg     720
ctgctacgtg ggttgcgaac gctggtgccg cgtatggagc tggcgcagcg caacgcgcag     780
```

```
gcgattgtga  aatacctgca  aacccagccg  ttggtgaaaa  aactgtatca  cccgtcgttg      840
ccggaaaatc  aggggcatga  aattgccgcg  cgccagcaaa  aaggctttgg  cgcaatgttg      900
agttttgaac  tggatggcga  tgagcagacg  ctgcgtcgtt  tcctgggcgg  gctgtcgttg      960
tttacgctgg  cggaatcatt  aggggagtg   gaaagtttaa  tctctcacgc  cgcaaccatg     1020
acacatgcag  gcatggcacc  agaagcgcgt  gctgccgccg  ggatctccga  gacgctgctg     1080
cgtatctcca  ccggtattga  agatggcgaa  gatttaattg  ccgacctgga  aaatggcttc     1140
cgggctgcaa  acaaggggta  a                                                  1161
```

<210> SEQ ID NO 11
<211> LENGTH: 310
<212> TYPE: PRT
<213> ORGANISM: Escherichia coli
<220> FEATURE:
<221> NAME/KEY: PEPTIDE
<222> LOCATION: (1)..(310)
<223> OTHER INFORMATION: thrB

<400> SEQUENCE: 11

```
Met Val Lys Val Tyr Ala Pro Ala Ser Ser Ala Asn Met Ser Val Gly
1               5                   10                  15

Phe Asp Val Leu Gly Ala Ala Val Thr Pro Val Asp Gly Ala Leu Leu
            20                  25                  30

Gly Asp Val Val Thr Val Glu Ala Ala Glu Thr Phe Ser Leu Asn Asn
        35                  40                  45

Leu Gly Arg Phe Ala Asp Lys Leu Pro Ser Glu Pro Arg Glu Asn Ile
    50                  55                  60

Val Tyr Gln Cys Trp Glu Arg Phe Cys Gln Glu Leu Gly Lys Gln Ile
65                  70                  75                  80

Pro Val Ala Met Thr Leu Glu Lys Asn Met Pro Ile Gly Ser Gly Leu
                85                  90                  95

Gly Ser Ser Ala Cys Ser Val Val Ala Ala Leu Met Ala Met Asn Glu
            100                 105                 110

His Cys Gly Lys Pro Leu Asn Asp Thr Arg Leu Leu Ala Leu Met Gly
        115                 120                 125

Glu Leu Glu Gly Arg Ile Ser Gly Ser Ile His Tyr Asp Asn Val Ala
    130                 135                 140

Pro Cys Phe Leu Gly Gly Met Gln Leu Met Ile Glu Glu Asn Asp Ile
145                 150                 155                 160

Ile Ser Gln Gln Val Pro Gly Phe Asp Glu Trp Leu Trp Val Leu Ala
                165                 170                 175

Tyr Pro Gly Ile Lys Val Ser Thr Ala Glu Ala Arg Ala Ile Leu Pro
            180                 185                 190

Ala Gln Tyr Arg Arg Gln Asp Cys Ile Ala His Gly Arg His Leu Ala
        195                 200                 205

Gly Phe Ile His Ala Cys Tyr Ser Arg Gln Pro Glu Leu Ala Ala Lys
    210                 215                 220

Leu Met Lys Asp Val Ile Ala Glu Pro Tyr Arg Glu Arg Leu Leu Pro
225                 230                 235                 240

Gly Phe Arg Gln Ala Arg Gln Ala Val Ala Glu Ile Gly Ala Val Ala
                245                 250                 255

Ser Gly Ile Ser Gly Ser Gly Pro Thr Leu Phe Ala Leu Cys Asp Lys
            260                 265                 270

Pro Glu Thr Ala Gln Arg Val Ala Asp Trp Leu Gly Lys Asn Tyr Leu
        275                 280                 285
```

Gln Asn Gln Glu Gly Phe Val His Ile Cys Arg Leu Asp Thr Ala Gly
    290                 295                 300

Ala Arg Val Leu Glu Asn
305                 310

<210> SEQ ID NO 12
<211> LENGTH: 933
<212> TYPE: DNA
<213> ORGANISM: Escherichia coli
<220> FEATURE:
<221> NAME/KEY: gene
<222> LOCATION: (1)..(933)
<223> OTHER INFORMATION: thrB

<400> SEQUENCE: 12
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300
aaaaaaaaaa aaaaaaaaaa aaaaaaaaaa aaaaaaaaaa aaaaaaaaaa aaaaaaaaaa     360
aaaaaaaaaa aaaaaaaaaa aaaaaaaaaa aaaaaaaaaa aaaaaaaaaa aaaaaaaaaa     420
aaaaaaaaaa aaaaaaaaaa aaaaaaaaaa aaaaaaaaaa aaaaaaaaaa aaaaaaaaaa     480
aaaaaaaaaa aaaaaaaaaa aaaaaaaaaa aaaaaaaaaa aaaaaaaaaa aaaaaaaaaa     540
aaaaaaaaaa aaaaaaaaaa aaaaaaaaaa aaaaaaaaaa aaaaaaaaaa aaaaaaaaaa     600
aaaaaaaaaa aaaaaaaaaa aaaaaaaaaa aaaaaaaaaa aaaaaaaaaa aaaaaaaaaa     660
aaaaaaaaaa aaaaaaaaaa aaaaaaaaaa aaaaaaaaaa aaaaaaaaaa aaaaaaaaaa     720
aaaaaaaaaa aaaaaaaaaa aaaaaaaaaa aaaaaaaaaa aaaaaaaaaa aaaaaaaaaa     780
aaaaaaaaaa aaaaaaaaaa aaaaaaaaaa aaaaaaaaaa aaaaaaaaaa aaaaaaaaaa     840
aaaaaaaaaa aaaaaaaaaa aaaaaaaaaa aaaaaaaaaa aaaaaaaaaa aaaaaaaaaa     900
aaaaaaaaaa aaaaaaaaaa aaaaaaaaaa aaa                                  933

<210> SEQ ID NO 13
<211> LENGTH: 379
<212> TYPE: PRT
<213> ORGANISM: Leptospira meyeri
<220> FEATURE:
<221> NAME/KEY: PEPTIDE
<222> LOCATION: (1)..(379)
<223> OTHER INFORMATION: homoserine O-acetyltransferase

<400> SEQUENCE: 13

Met Pro Thr Ser Glu Gln Asn Glu Phe Ser His Gly Ser Val Gly Val
1               5                   10                  15

Val Tyr Thr Gln Ser Ile Arg Phe Glu Ser Leu Thr Leu Glu Gly Gly
            20                  25                  30

Glu Thr Ile Thr Pro Leu Glu Ile Ala Tyr Glu Thr Tyr Gly Thr Leu
        35                  40                  45

Asn Glu Lys Lys Asp Asn Ala Ile Leu Val Cys His Ala Leu Ser Gly
    50                  55                  60

Asp Ala His Ala Ala Gly Phe His Glu Gly Asp Lys Arg Pro Gly Trp
65                  70                  75                  80

Trp Asp Tyr Tyr Ile Gly Pro Gly Lys Ser Phe Asp Thr Asn Arg Tyr

```
            85                  90                  95
Phe Ile Ile Ser Ser Asn Val Ile Gly Gly Cys Lys Gly Ser Gly
            100                 105                 110

Pro Leu Thr Ile Asn Gly Lys Asn Gly Lys Pro Phe Gln Ser Thr Phe
        115                 120                 125

Pro Phe Val Ser Ile Gly Asp Met Val Asn Ala Gln Glu Lys Leu Ile
    130                 135                 140

Ser His Phe Gly Ile His Lys Leu Phe Ala Val Ala Gly Gly Ser Met
145                 150                 155                 160

Gly Gly Met Gln Ala Leu Gln Trp Ser Val Ala Tyr Pro Asp Arg Leu
                165                 170                 175

Lys Asn Cys Ile Val Met Ala Ser Ser Glu His Ser Ala Gln Gln
            180                 185                 190

Ile Ala Phe Asn Glu Val Gly Arg Gln Ala Ile Leu Ser Asp Pro Asn
        195                 200                 205

Trp Asn Gln Gly Leu Tyr Thr Gln Glu Asn Arg Pro Ser Lys Gly Leu
    210                 215                 220

Ala Leu Ala Arg Met Met Gly His Ile Thr Tyr Leu Ser Asp Glu Met
225                 230                 235                 240

Met Arg Glu Lys Phe Gly Arg Lys Pro Pro Lys Gly Asn Ile Gln Ser
                245                 250                 255

Thr Asp Phe Ala Val Gly Ser Tyr Leu Ile Tyr Gln Gly Glu Ser Phe
            260                 265                 270

Val Asp Arg Phe Asp Ala Asn Ser Tyr Ile Tyr Val Thr Lys Ala Leu
        275                 280                 285

Asp His Phe Ser Leu Gly Thr Gly Lys Glu Leu Thr Lys Val Leu Ala
    290                 295                 300

Lys Val Arg Cys Arg Phe Leu Val Val Ala Tyr Thr Ser Asp Trp Leu
305                 310                 315                 320

Tyr Pro Pro Tyr Gln Ser Glu Glu Ile Val Lys Ser Leu Glu Val Asn
                325                 330                 335

Ala Val Pro Val Ser Phe Val Glu Leu Asn Asn Pro Ala Gly Arg His
            340                 345                 350

Asp Ser Phe Leu Leu Pro Ser Glu Gln Gln Asp Ser Ile Leu Arg Asp
        355                 360                 365

Phe Leu Ser Ser Thr Asp Glu Gly Val Phe Leu
    370                 375

<210> SEQ ID NO 14
<211> LENGTH: 379
<212> TYPE: PRT
<213> ORGANISM: Corynebacterium glutamicum
<220> FEATURE:
<221> NAME/KEY: PEPTIDE
<222> LOCATION: (1)..(379)
<223> OTHER INFORMATION: homoserine O-acetyltransferase

<400> SEQUENCE: 14

Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60
```

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
            115                 120                 125

Asp Ala Leu Gly Ile Thr Thr Val Ala Val Val Leu Leu Gly Gly
        130                 135                 140

Ser Met Gly Gly Ala Arg Thr Leu Glu Trp Ala Ala Met Tyr Pro Glu
145                 150                 155                 160

Thr Val Gly Ala Ala Ala Val Leu Ala Val Ser Ala Arg Ala Ser Ala
                165                 170                 175

Trp Gln Ile Gly Ile Gln Ser Ala Gln Ile Lys Ala Ile Glu Asn Asp
            180                 185                 190

His His Trp His Glu Gly Asn Tyr Tyr Glu Ser Gly Cys Asn Pro Ala
        195                 200                 205

Thr Gly Leu Gly Ala Ala Arg Arg Ile Ala His Leu Thr Tyr Arg Gly
    210                 215                 220

Glu Leu Glu Ile Asp Glu Arg Phe Gly Thr Lys Ala Gln Lys Asn Glu
225                 230                 235                 240

Asn Pro Leu Gly Pro Tyr Arg Lys Pro Asp Gln Arg Phe Ala Val Glu
                245                 250                 255

Ser Tyr Leu Asp Tyr Gln Ala Asp Lys Leu Val Gln Arg Phe Asp Ala
            260                 265                 270

Gly Ser Tyr Val Leu Leu Thr Asp Ala Leu Asn Arg His Asp Ile Gly
        275                 280                 285

Arg Asp Arg Gly Gly Leu Asn Lys Ala Leu Glu Ser Ile Lys Val Pro
    290                 295                 300

Val Leu Val Ala Gly Val Asp Thr Asp Ile Leu Tyr Pro Tyr His Gln
305                 310                 315                 320

Gln Glu His Leu Ser Arg Asn Leu Gly Asn Leu Leu Ala Met Ala Lys
                325                 330                 335

Ile Val Ser Pro Val Gly His Asp Ala Phe Leu Thr Glu Ser Arg Gln
            340                 345                 350

Met Asp Arg Ile Val Arg Asn Phe Phe Ser Leu Ile Ser Pro Asp Glu
        355                 360                 365

Asp Asn Pro Ser Thr Tyr Ile Glu Phe Tyr Ile
    370                 375

<210> SEQ ID NO 15
<211> LENGTH: 334
<212> TYPE: PRT
<213> ORGANISM: Deinococcus radiodurans
<220> FEATURE:
<221> NAME/KEY: PEPTIDE
<222> LOCATION: (1)..(334)
<223> OTHER INFORMATION: homoserine O-acetyltransferase

<400> SEQUENCE: 15

Met Thr Ala Val Leu Ala Gly His Ala Ser Ala Leu Leu Leu Thr Glu
1               5                   10                  15

Glu Pro Asp Cys Ser Gly Pro Gln Thr Val Val Leu Phe Arg Arg Glu
            20                  25                  30

```
Pro Leu Leu Leu Asp Cys Gly Arg Ala Leu Ser Asp Val Arg Val Ala
                35                  40                  45

Phe His Thr Tyr Gly Thr Pro Arg Ala Asp Ala Thr Leu Val Leu His
 50                  55                  60

Ala Leu Thr Gly Asp Ser Ala Val His Glu Trp Trp Pro Asp Phe Leu
 65                  70                  75                  80

Gly Ala Gly Arg Pro Leu Asp Pro Ala Asp Asp Tyr Val Val Cys Ala
                 85                  90                  95

Asn Val Leu Gly Gly Cys Ala Gly Thr Thr Ser Ala Ala Glu Leu Ala
                100                 105                 110

Ala Thr Cys Ser Gly Pro Val Pro Leu Ser Leu Arg Asp Met Ala Arg
                115                 120                 125

Val Gly Arg Ala Leu Leu Asp Ser Leu Gly Val Arg Arg Val Arg Val
                130                 135                 140

Ile Gly Ala Ser Met Gly Gly Met Leu Ala Tyr Ala Trp Leu Leu Glu
145                 150                 155                 160

Cys Pro Asp Leu Val Glu Lys Ala Val Ile Ile Gly Ala Pro Ala Arg
                165                 170                 175

His Ser Pro Trp Ala Ile Gly Leu Asn Thr Ala Ala Arg Ser Ala Ile
                180                 185                 190

Ala Leu Ala Pro Gly Gly Glu Gly Leu Lys Val Ala Arg Gln Ile Ala
                195                 200                 205

Met Leu Ser Tyr Arg Ser Pro Glu Ser Leu Ser Arg Thr Gln Ala Gly
                210                 215                 220

Gln Arg Val Pro Gly Val Pro Ala Val Thr Ser Tyr Leu His Tyr Gln
225                 230                 235                 240

Gly Glu Lys Leu Ala Ala Arg Phe Asp Glu Gln Thr Tyr Cys Ala Leu
                245                 250                 255

Thr Trp Ala Met Asp Ala Phe Gln Pro Ser Ser Ala Asp Leu Lys Ala
                260                 265                 270

Val Arg Ala Pro Val Leu Val Val Gly Ile Ser Ser Asp Leu Leu Tyr
                275                 280                 285

Pro Ala Ala Glu Val Arg Ala Cys Ala Ala Glu Leu Pro His Ala Asp
                290                 295                 300

Tyr Trp Glu Leu Gly Ser Ile His Gly His Asp Ala Phe Leu Met Asp
305                 310                 315                 320

Pro Gln Asp Leu Pro Glu Arg Val Gly Ala Phe Leu Arg Ser
                325                 330

<210> SEQ ID NO 16
<211> LENGTH: 309
<212> TYPE: PRT
<213> ORGANISM: Escherichia coli
<220> FEATURE:
<221> NAME/KEY: PEPTIDE
<222> LOCATION: (1)..(309)
<223> OTHER INFORMATION: homoserine O-succinyl transferase

<400> SEQUENCE: 16

Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Ser Gly Gln Glu
                20                  25                  30

Ile Arg Pro Leu Lys Val Leu Ile Leu Asn Leu Met Pro Lys Lys Ile
                35                  40                  45

Glu Thr Glu Asn Gln Phe Leu Arg Leu Leu Ser Asn Ser Pro Leu Gln
```

```
Val Asp Ile Gln Leu Leu Arg Ile Asp Ser Arg Glu Ser Arg Asn Thr
 65                  70                  75                  80

Pro Ala Glu His Leu Asn Asn Phe Tyr Cys Asn Phe Glu Asp Ile Gln
                 85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Glu Gly Asp Ala Tyr Leu Phe Ala Ser
210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
            245                 250                 255

Pro Asp Val Pro Tyr Asn Tyr Phe Pro His Asn Asp Pro Gln Asn Thr
        260                 265                 270

Pro Arg Ala Ser Trp Arg Ser His Gly Asn Leu Leu Phe Thr Asn Trp
            275                 280                 285

Leu Asn Tyr Tyr Val Tyr Gln Ile Thr Pro Tyr Asp Leu Arg His Met
            290                 295                 300

Asn Pro Thr Leu Asp
305

<210> SEQ ID NO 17
<211> LENGTH: 309
<212> TYPE: PRT
<213> ORGANISM: Artificial Sequence
<220> FEATURE:
<223> OTHER INFORMATION: Variant polypeptide having homoserine o-acetyl
      transferase activity, metA EL

<400> SEQUENCE: 17

Met Pro Ile Arg Val Pro Asp Glu Leu Pro Ala Val Asn Phe Leu Arg
 1               5                  10                  15

Glu Glu Asn Val Phe Val Met Thr Thr Ser Arg Ala Ser Gly Gln Glu
                 20                  25                  30

Ile Arg Pro Leu Lys Val Leu Ile Leu Asn Leu Met Pro Lys Lys Ile
             35                  40                  45

Glu Thr Glu Asn Gln Phe Leu Arg Leu Ser Asn Ser Pro Leu Gln
 50                  55                  60

Val Asp Ile Gln Leu Leu Arg Ile Asp Ser Arg Glu Ser Arg Asn Thr
 65                  70                  75                  80

Pro Ala Glu His Leu Asn Asn Phe Tyr Cys Asn Phe Glu Asp Ile Gln
                 85                  90                  95
```

```
Asp Gln Asn Phe Asp Gly Leu Ile Val Thr Gly Ala Pro Leu Glu Leu
                100                 105                 110

Val Glu Phe Asn Asp Val Ala Tyr Trp Pro Gln Ile Lys Gln Val Leu
            115                 120                 125

Glu Trp Ser Lys Asp His Val Thr Ser Thr Leu Phe Val Cys Trp Ala
        130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Glu Gly Asp Ala Tyr Leu Phe Ala Ser
210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
        275                 280                 285

Leu Asn Tyr Tyr Val Tyr Gln Ile Thr Pro Tyr Asp Leu Arg His Met
290                 295                 300

Asn Pro Thr Leu Asp
305

<210> SEQ ID NO 18
<211> LENGTH: 309
<212> TYPE: PRT
<213> ORGANISM: Artificial Sequence
<220> FEATURE:
<223> OTHER INFORMATION: Variant polypeptide having homoserine O-acetyl
      transferase activity, metA ET

<400> SEQUENCE: 18

Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Glu Thr
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
    130                 135                 140
```

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Gly Asp Ala Tyr Leu Phe Ala Ser
    210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
        275                 280                 285

Leu Asn Tyr Tyr Val Tyr Gln Ile Thr Pro Tyr Asp Leu Arg His Met
    290                 295                 300

Asn Pro Thr Leu Asp
305

<210> SEQ ID NO 19
<211> LENGTH: 309
<212> TYPE: PRT
<213> ORGANISM: Artificial Sequence
<220> FEATURE:
<223> OTHER INFORMATION: Variant polypeptide having homoserine O-acetyl
      transferase activity, metA EH

<400> SEQUENCE: 19

Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Ser Gly Gln Glu
                20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Glu His
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
    130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser

```
            180                 185                 190
Arg Tyr Ala Asp Phe Pro Ala Ala Leu Ile Arg Asp Tyr Thr Asp Leu
        195                 200                 205

Glu Ile Leu Ala Glu Thr Glu Glu Gly Asp Ala Tyr Leu Phe Ala Ser
    210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
            245                 250                 255

Pro Asp Val Pro Tyr Asn Tyr Phe Pro His Asn Asp Pro Gln Asn Thr
        260                 265                 270

Pro Arg Ala Ser Trp Arg Ser His Gly Asn Leu Leu Phe Thr Asn Trp
    275                 280                 285

Leu Asn Tyr Tyr Val Tyr Gln Ile Thr Pro Tyr Asp Leu Arg His Met
    290                 295                 300

Asn Pro Thr Leu Asp
305

<210> SEQ ID NO 20
<211> LENGTH: 883
<212> TYPE: PRT
<213> ORGANISM: Escherichia coli
<220> FEATURE:
<221> NAME/KEY: PEPTIDE
<222> LOCATION: (1)..(883)
<223> OTHER INFORMATION: phosphoenolpyruvate carboxylase

<400> SEQUENCE: 20

Met Asn Glu Gln Tyr Ser Ala Leu Arg Ser Asn Val Ser Met Leu Gly
1               5                   10                  15

Lys Val Leu Gly Glu Thr Ile Lys Asp Ala Leu Gly Glu His Ile Leu
            20                  25                  30

Glu Arg Val Glu Thr Ile Arg Lys Leu Ser Lys Ser Ser Arg Ala Gly
        35                  40                  45

Asn Asp Ala Asn Arg Gln Glu Leu Leu Thr Thr Leu Gln Asn Leu Ser
    50                  55                  60

Asn Asp Glu Leu Leu Pro Val Ala Arg Ala Phe Ser Gln Phe Leu Asn
65                  70                  75                  80

Leu Ala Asn Thr Ala Glu Gln Tyr His Ser Ile Ser Pro Lys Gly Glu
                85                  90                  95

Ala Ala Ser Asn Pro Glu Val Ile Ala Arg Thr Leu Arg Lys Leu Lys
            100                 105                 110

Asn Gln Pro Glu Leu Ser Glu Asp Thr Ile Lys Lys Ala Val Glu Ser
        115                 120                 125

Leu Ser Leu Glu Leu Val Leu Thr Ala His Pro Thr Glu Ile Thr Arg
    130                 135                 140

Arg Thr Leu Ile His Lys Met Val Glu Val Asn Ala Cys Leu Lys Gln
145                 150                 155                 160

Leu Asp Asn Lys Asp Ile Ala Asp Tyr Glu His Asn Gln Leu Met Arg
                165                 170                 175

Arg Leu Arg Gln Leu Ile Ala Gln Ser Trp His Thr Asp Glu Ile Arg
            180                 185                 190

Lys Leu Arg Pro Ser Pro Val Asp Glu Ala Lys Trp Gly Phe Ala Val
        195                 200                 205

Val Glu Asn Ser Leu Trp Gln Gly Val Pro Asn Tyr Leu Arg Glu Leu
    210                 215                 220
```

-continued

```
Asn Glu Gln Leu Glu Glu Asn Leu Gly Tyr Lys Leu Pro Val Glu Phe
225                 230                 235                 240

Val Pro Val Arg Phe Thr Ser Trp Met Gly Gly Asp Arg Asp Gly Asn
            245                 250                 255

Pro Asn Val Thr Ala Asp Ile Thr Arg His Val Leu Leu Leu Ser Arg
                260                 265                 270

Trp Lys Ala Thr Asp Leu Phe Leu Lys Asp Ile Gln Val Leu Val Ser
            275                 280                 285

Glu Leu Ser Met Val Glu Ala Thr Pro Glu Leu Leu Ala Leu Val Gly
        290                 295                 300

Glu Glu Gly Ala Ala Glu Pro Tyr Arg Tyr Leu Met Lys Asn Leu Arg
305                 310                 315                 320

Ser Arg Leu Met Ala Thr Gln Ala Trp Leu Glu Ala Arg Leu Lys Gly
                325                 330                 335

Glu Glu Leu Pro Lys Pro Glu Gly Leu Leu Thr Gln Asn Glu Glu Leu
            340                 345                 350

Trp Glu Pro Leu Tyr Ala Cys Tyr Gln Ser Leu Gln Ala Cys Gly Met
        355                 360                 365

Gly Ile Ile Ala Asn Gly Asp Leu Leu Asp Thr Leu Arg Arg Val Lys
370                 375                 380

Cys Phe Gly Val Pro Leu Val Arg Ile Asp Ile Arg Gln Glu Ser Thr
385                 390                 395                 400

Arg His Thr Glu Ala Leu Gly Glu Leu Thr Arg Tyr Leu Gly Ile Gly
                405                 410                 415

Asp Tyr Glu Ser Trp Ser Glu Ala Asp Lys Gln Ala Phe Leu Ile Arg
            420                 425                 430

Glu Leu Asn Ser Lys Arg Pro Leu Leu Pro Arg Asn Trp Gln Pro Ser
        435                 440                 445

Ala Glu Thr Arg Glu Val Leu Asp Thr Cys Gln Val Ile Ala Glu Ala
            450                 455                 460

Pro Gln Gly Ser Ile Ala Ala Tyr Val Ile Ser Met Ala Lys Thr Pro
465                 470                 475                 480

Ser Asp Val Leu Ala Val His Leu Leu Leu Lys Glu Ala Gly Ile Gly
                485                 490                 495

Phe Ala Met Pro Val Ala Pro Leu Phe Glu Thr Leu Asp Asp Leu Asn
            500                 505                 510

Asn Ala Asn Asp Val Met Thr Gln Leu Leu Asn Ile Asp Trp Tyr Arg
        515                 520                 525

Gly Leu Ile Gln Gly Lys Gln Met Val Met Ile Gly Tyr Ser Asp Ser
        530                 535                 540

Ala Lys Asp Ala Gly Val Met Ala Ala Ser Trp Ala Gln Tyr Gln Ala
545                 550                 555                 560

Gln Asp Ala Leu Ile Lys Thr Cys Glu Lys Ala Gly Ile Glu Leu Thr
                565                 570                 575

Leu Phe His Gly Arg Gly Gly Ser Ile Gly Arg Gly Gly Ala Pro Ala
            580                 585                 590

His Ala Ala Leu Leu Ser Gln Pro Pro Gly Ser Leu Lys Gly Gly Leu
        595                 600                 605

Arg Val Thr Glu Gln Gly Glu Met Ile Arg Phe Lys Tyr Gly Leu Pro
        610                 615                 620

Glu Ile Thr Val Ser Ser Leu Ser Leu Tyr Thr Gly Ala Ile Leu Glu
625                 630                 635                 640
```

Ala Asn Leu Leu Pro Pro Glu Pro Lys Glu Ser Trp Arg Arg Ile
              645                 650                 655

Met Asp Glu Leu Ser Val Ile Ser Cys Asp Val Tyr Arg Gly Tyr Val
        660                 665                 670

Arg Glu Asn Lys Asp Phe Val Pro Tyr Phe Arg Ser Ala Thr Pro Glu
            675                 680                 685

Gln Glu Leu Gly Lys Leu Pro Leu Gly Ser Arg Pro Ala Lys Arg Arg
        690                 695                 700

Pro Thr Gly Gly Val Glu Ser Leu Arg Ala Ile Pro Trp Ile Phe Ala
705                 710                 715                 720

Trp Thr Gln Asn Arg Leu Met Leu Pro Ala Trp Leu Gly Ala Gly Thr
                725                 730                 735

Ala Leu Gln Lys Val Val Glu Asp Gly Lys Gln Ser Glu Leu Glu Ala
            740                 745                 750

Met Cys Arg Asp Trp Pro Phe Phe Ser Thr Arg Leu Gly Met Leu Glu
        755                 760                 765

Met Val Phe Ala Lys Ala Asp Leu Trp Leu Ala Glu Tyr Tyr Asp Gln
    770                 775                 780

Arg Leu Val Asp Lys Ala Leu Trp Pro Leu Gly Lys Glu Leu Arg Asn
785                 790                 795                 800

Leu Gln Glu Glu Asp Ile Lys Val Val Leu Ala Ile Ala Asn Asp Ser
                805                 810                 815

His Leu Met Ala Asp Leu Pro Trp Ile Ala Glu Ser Ile Gln Leu Arg
            820                 825                 830

Asn Ile Tyr Thr Asp Pro Leu Asn Val Leu Gln Ala Glu Leu Leu His
        835                 840                 845

Arg Ser Arg Gln Ala Glu Lys Glu Gly Gln Glu Pro Asp Pro Arg Val
850                 855                 860

Glu Gln Ala Leu Met Val Thr Ile Ala Gly Ile Ala Ala Gly Met Arg
865                 870                 875                 880

Asn Thr Gly

<210> SEQ ID NO 21
<211> LENGTH: 396
<212> TYPE: PRT
<213> ORGANISM: Escherichia coli
<220> FEATURE:
<221> NAME/KEY: PEPTIDE
<222> LOCATION: (1)..(396)
<223> OTHER INFORMATION: aspartate aminotransferase

<400> SEQUENCE: 21

Met Phe Glu Asn Ile Thr Ala Ala Pro Ala Asp Pro Ile Leu Gly Leu
1               5                   10                  15

Ala Asp Leu Phe Arg Ala Asp Glu Arg Pro Gly Lys Ile Asn Leu Gly
            20                  25                  30

Ile Gly Val Tyr Lys Asp Glu Thr Gly Lys Thr Pro Val Leu Thr Ser
        35                  40                  45

Val Lys Lys Ala Glu Gln Tyr Leu Leu Glu Asn Glu Thr Thr Lys Asn
    50                  55                  60

Tyr Leu Gly Ile Asp Gly Ile Pro Glu Phe Gly Arg Cys Thr Gln Glu
65                  70                  75                  80

Leu Leu Phe Gly Lys Gly Ser Ala Leu Ile Asn Asp Lys Arg Ala Arg
                85                  90                  95

Thr Ala Gln Thr Pro Gly Gly Thr Gly Ala Leu Arg Val Ala Ala Asp
            100                 105                 110

Phe Leu Ala Lys Asn Thr Ser Val Lys Arg Val Trp Val Ser Asn Pro
              115                 120                 125

Ser Trp Pro Asn His Lys Ser Val Phe Asn Ser Ala Gly Leu Glu Val
    130                 135                 140

Arg Glu Tyr Ala Tyr Tyr Asp Ala Glu Asn His Thr Leu Asp Phe Asp
145                 150                 155                 160

Ala Leu Ile Asn Ser Leu Asn Glu Ala Gln Ala Gly Asp Val Val Leu
                165                 170                 175

Phe His Gly Cys Cys His Asn Pro Thr Gly Ile Asp Pro Thr Leu Glu
            180                 185                 190

Gln Trp Gln Thr Leu Ala Gln Leu Ser Val Glu Lys Gly Trp Leu Pro
        195                 200                 205

Leu Phe Asp Phe Ala Tyr Gln Gly Phe Ala Arg Gly Leu Glu Glu Asp
    210                 215                 220

Ala Glu Gly Leu Arg Ala Phe Ala Ala Met His Lys Glu Leu Ile Val
225                 230                 235                 240

Ala Ser Ser Tyr Ser Lys Asn Phe Gly Leu Tyr Asn Glu Arg Val Gly
                245                 250                 255

Ala Cys Thr Leu Val Ala Ala Asp Ser Glu Thr Val Asp Arg Ala Phe
            260                 265                 270

Ser Gln Met Lys Ala Ala Ile Arg Ala Asn Tyr Ser Asn Pro Pro Ala
        275                 280                 285

His Gly Ala Ser Val Val Ala Thr Ile Leu Ser Asn Asp Ala Leu Arg
    290                 295                 300

Ala Ile Trp Glu Gln Glu Leu Thr Asp Met Arg Gln Arg Ile Gln Arg
305                 310                 315                 320

Met Arg Gln Leu Phe Val Asn Thr Leu Gln Glu Lys Gly Ala Asn Arg
                325                 330                 335

Asp Phe Ser Phe Ile Ile Lys Gln Asn Gly Met Phe Ser Phe Ser Gly
            340                 345                 350

Leu Thr Lys Glu Gln Val Leu Arg Leu Arg Glu Glu Phe Gly Val Tyr
        355                 360                 365

Ala Val Ala Ser Gly Arg Val Asn Val Ala Gly Met Thr Pro Asp Asn
    370                 375                 380

Met Ala Pro Leu Cys Glu Ala Ile Val Ala Val Leu
385                 390                 395

<210> SEQ ID NO 22
<211> LENGTH: 367
<212> TYPE: PRT
<213> ORGANISM: Escherichia coli
<220> FEATURE:
<221> NAME/KEY: PEPTIDE
<222> LOCATION: (1)..(367)
<223> OTHER INFORMATION: aspartate-semialdehyde dehydrogenase

<400> SEQUENCE: 22

Met Lys Asn Val Gly Phe Ile Gly Trp Arg Gly Met Val Gly Ser Val
1               5                   10                  15

Leu Met Gln Arg Met Val Glu Glu Arg Asp Phe Asp Ala Ile Arg Pro
                20                  25                  30

Val Phe Phe Ser Thr Ser Gln Leu Gly Gln Ala Ala Pro Ser Phe Gly
            35                  40                  45

Gly Thr Thr Gly Thr Leu Gln Asp Ala Phe Asp Leu Glu Ala Leu Lys
        50                  55                  60

```
Ala Leu Asp Ile Ile Val Thr Cys Gln Gly Gly Asp Tyr Thr Asn Glu
 65                  70                  75                  80

Ile Tyr Pro Lys Leu Arg Glu Ser Gly Trp Gln Gly Tyr Trp Ile Asp
             85                  90                  95

Ala Ala Ser Ser Leu Arg Met Lys Asp Asp Ala Ile Ile Ile Leu Asp
            100                 105                 110

Pro Val Asn Gln Asp Val Ile Thr Asp Gly Leu Asn Asn Gly Ile Arg
        115                 120                 125

Thr Phe Val Gly Gly Asn Cys Thr Val Ser Leu Met Leu Met Ser Leu
    130                 135                 140

Gly Gly Leu Phe Ala Asn Asp Leu Val Asp Trp Val Ser Val Ala Thr
145                 150                 155                 160

Tyr Gln Ala Ala Ser Gly Gly Ala Arg His Met Arg Glu Leu Leu
                165                 170                 175

Thr Gln Met Gly His Leu Tyr Gly His Val Ala Asp Glu Leu Ala Thr
            180                 185                 190

Pro Ser Ser Ala Ile Leu Asp Ile Glu Arg Lys Val Thr Thr Leu Thr
        195                 200                 205

Arg Ser Gly Glu Leu Pro Val Asp Asn Phe Gly Val Pro Leu Ala Gly
210                 215                 220

Ser Leu Ile Pro Trp Ile Asp Lys Gln Leu Asp Asn Gly Gln Ser Arg
225                 230                 235                 240

Glu Glu Trp Lys Gly Gln Ala Glu Thr Asn Lys Ile Leu Asn Thr Ser
                245                 250                 255

Ser Val Ile Pro Val Asp Gly Leu Cys Val Arg Val Gly Ala Leu Arg
            260                 265                 270

Cys His Ser Gln Ala Phe Thr Ile Lys Leu Lys Lys Asp Val Ser Ile
        275                 280                 285

Pro Thr Val Glu Glu Leu Leu Ala Ala His Asn Pro Trp Ala Lys Val
290                 295                 300

Val Pro Asn Asp Arg Glu Ile Thr Met Arg Glu Leu Thr Pro Ala Ala
305                 310                 315                 320

Val Thr Gly Thr Leu Thr Thr Pro Val Gly Arg Leu Arg Lys Leu Asn
                325                 330                 335

Met Gly Pro Glu Phe Leu Ser Ala Phe Thr Val Gly Asp Gln Leu Leu
            340                 345                 350

Trp Gly Ala Ala Glu Pro Leu Arg Arg Met Leu Arg Gln Leu Ala
        355                 360                 365

<210> SEQ ID NO 23
<211> LENGTH: 933
<212> TYPE: DNA
<213> ORGANISM: Escherichia coli
<220> FEATURE:
<221> NAME/KEY: gene
<222> LOCATION: (1)..(933)
<223> OTHER INFORMATION: homoserine O-succinyl transferase

<400> SEQUENCE: 23
atggttaaag tttatgcccc ggcttccagt gccaatatga gcgtcgggtt tgatgtgctc    60
ggggcggcgg tgacacctgt tgatggtgca ttgctcggag atgtagtcac ggttgaggcg   120
gcagagacat tcagtctcaa caacctcgga cgctttgccg ataagctgcc gtcagaacca   180
cgggaaaata tcgtttatca gtgctggag cgttttttgc aggaactggg taagcaaatt   240
ccagtggcga tgaccctgga aaagaatatg ccgatcggtt cgggcttagg ctccagtgcc   300
```

```
tgttcggtgg tcgcggcgct gatggcgatg aatgaacact gcggcaagcc gcttaatgac      360
actcgtttgc tggctttgat gggcgagctg gaaggccgta tctccggcag cattcattac      420
gacaacgtgg caccgtgttt tctcggtggt atgcagttga tgatcgaaga aaacgacatc      480
atcagccagc aagtgccagg gtttgatgag tggctgtggg tgctggcgta tccggggatt      540
aaagtctcga cggcagaagc cagggctatt ttaccggcgc agtatcgccg ccaggattgc      600
attgcgcacg ggcgacatct ggcaggcttc attcacgcct gctattcccg tcagcctgag      660
cttgccgcga agctgatgaa agatgttatc gctgaaccct accgtgaacg gttactgcca      720
ggcttccggc aggcgcggca ggcggtcgcg gaaatcggcg cggtagcgag cggtatctcc      780
ggctccggcc cgaccttgtt cgctctgtgt gacaagccgg aaaccgccca gcgcgttgcc      840
gactggttgg gtaagaacta cctgcaaaat caggaaggtt ttgttcatat ttgccggctg      900
gatacggcgg gcgcacgagt actggaaaac taa                                    933

<210> SEQ ID NO 24
<211> LENGTH: 930
<212> TYPE: DNA
<213> ORGANISM: Artificial Sequence
<220> FEATURE:
<223> OTHER INFORMATION: Variant polypeptide having homoserine O-acetyl
      transferase activity, metA EL

<400> SEQUENCE: 24
atgccgattc gtgtgccgga cgagctaccc gccgtcaatt tcttgcgtga agaaaacgtc       60
tttgtgatga caacttctcg tgcgtctggt caggaaattc gtccacttaa ggttctgatc      120
cttaacctga tgccgaagaa gattgaaact gaaaatcagt ttctgcgcct gctttcaaac      180
tcacctttgc aggtcgatat tcagctgttg cgcatcgatt ccgtgaatc gcgcaacacg      240 cccgcagagc atctgaacaa cttctactgt aactttgaag atattcagga tcagaacttt      300
gacggtttga ttgtaactgg tgcgccgctg gaactggtgg agtttaatga tgtcgcttac      360
tggccgcaga tcaaacaggt gctggagtgg tcgaaagatc acgtcacctc gacgctgttt      420
gtctgctggg cggtacaggc cgcgctcaat atcctctacg gcattcctaa gcaaactcgc      480
accgaaaaac tctctggcgt ttacgagcat catattctcc atcctcatgc gcttctgacg      540
cgtggctttg atgattcatt cctggcaccg cattcgcgct atgctgactt tccggcagcg      600
ttgattcgtg attacaccga tctggaaatt ctggcagaga cggaagaagg ggatgcatat      660
ctgtttgcca gtaaagataa gcgcattgcc tttgtgacgg ccatcccga atatgatgcg      720 caaacgctgg cgcaggaatt tttccgcgat gtggaagccg gactagaccc ggatgtaccg      780
tataactatt tcccgcacaa tgatccgcaa atacaccgc gagcgagctg gcgtagtcac      840
ggtaatttac tgtttaccaa ctggctcaac tattacgtct accagatcac gccatacgat      900
ctacggcaca tgaatccaac gctggattaa                                        930

<210> SEQ ID NO 25
<211> LENGTH: 930
<212> TYPE: DNA
<213> ORGANISM: Artificial Sequence
<220> FEATURE:
<223> OTHER INFORMATION: Variant polypeptide having homoserine O-acetyl
      transferase activity, metA ET

<400> SEQUENCE: 25
atgccgattc gtgtgccgga cgagctaccc gccgtcaatt tcttgcgtga agaaaacgtc       60
tttgtgatga caacttctcg tgcgtctggt caggaaattc gtccacttaa ggttctgatc      120
```

```
cttaacctga tgccgaagaa gattgaaact gaaaatcagt ttctgcgcct gctttcaaac    180
tcacctttgc aggtcgatat tcagctgttg cgcatcgatt cccgtgaatc gcgcaacacg    240
cccgcagagc atctgaacaa cttctactgt aactttgaag atattcagga tcagaacttt    300
gacggtttga ttgtaactgg tgcgccgctg aaaccgtgg agtttaatga tgtcgcttac     360
tggccgcaga tcaaacaggt gctggagtgg tcgaaagatc acgtcacctc gacgctgttt    420
gtctgctggg cggtacaggc cgcgctcaat atcctctacg gcattcctaa gcaaactcgc    480
accgaaaaac tctctggcgt ttacgagcat catattctcc atcctcatgc gcttctgacg    540
cgtggctttg atgattcatt cctggcaccg cattcgcgct atgctgactt tccggcagcg    600
ttgattcgtg attacaccga tctggaaatt ctggcagaga cggaagaagg ggatgcatat    660
ctgtttgcca gtaaagataa gcgcattgcc tttgtgacgg ccatcccga atatgatgcg     720 caaacgctgg cgcaggaatt tttccgcgat gtggaagccg gactagaccc ggatgtaccg    780
tataactatt tcccgcacaa tgatccgcaa aatacaccgc gagcgagctg gcgtagtcac    840
ggtaatttac tgtttaccaa ctggctcaac tattacgtct accagatcac gccatacgat    900
ctacggcaca tgaatccaac gctggattaa                                     930

<210> SEQ ID NO 26
<211> LENGTH: 930
<212> TYPE: DNA
<213> ORGANISM: Artificial Sequence
<220> FEATURE:
<223> OTHER INFORMATION: Variant polypeptide having homoserine O-acetyl
      transferase activity, metA EH

<400> SEQUENCE: 26
atgccgattc gtgtgccgga cgagctaccc gccgtcaatt tcttgcgtga agaaaacgtc     60
tttgtgatga caacttctcg tgcgtctggt caggaaattc gtccacttaa ggttctgatc    120
cttaacctga tgccgaagaa gattgaaact gaaaatcagt ttctgcgcct gctttcaaac    180
tcacctttgc aggtcgatat tcagctgttg cgcatcgatt cccgtgaatc gcgcaacacg    240
cccgcagagc atctgaacaa cttctactgt aactttgaag atattcagga tcagaacttt    300
gacggtttga ttgtaactgg tgcgccgctg aacatgtgg agtttaatga tgtcgcttac     360
tggccgcaga tcaaacaggt gctggagtgg tcgaaagatc acgtcacctc gacgctgttt    420
gtctgctggg cggtacaggc cgcgctcaat atcctctacg gcattcctaa gcaaactcgc    480
accgaaaaac tctctggcgt ttacgagcat catattctcc atcctcatgc gcttctgacg    540
cgtggctttg atgattcatt cctggcaccg cattcgcgct atgctgactt tccggcagcg    600
ttgattcgtg attacaccga tctggaaatt ctggcagaga cggaagaagg ggatgcatat    660
ctgtttgcca gtaaagataa gcgcattgcc tttgtgacgg ccatcccga atatgatgcg     720 caaacgctgg cgcaggaatt tttccgcgat gtggaagccg gactagaccc ggatgtaccg    780
tataactatt tcccgcacaa tgatccgcaa aatacaccgc gagcgagctg gcgtagtcac    840
ggtaatttac tgtttaccaa ctggctcaac tattacgtct accagatcac gccatacgat    900
ctacggcaca tgaatccaac gctggattaa                                     930

<210> SEQ ID NO 27
<211> LENGTH: 2652
<212> TYPE: DNA
<213> ORGANISM: Escherichia coli
<220> FEATURE:
<221> NAME/KEY: gene
```

```
<222> LOCATION: (1)..(2652)
<223> OTHER INFORMATION: phosphoenolpyruvate carboxylase

<400> SEQUENCE: 27
atgaacgaac aatattccgc attgcgtagt aatgtcagta tgctcggcaa agtgctggga      60
gaaaccatca aggatgcgtt gggagaacac attcttgaac gcgtagaaac tatccgtaag     120
ttgtcgaaat cttcacgcgc tggcaatgat gctaaccgcc aggagttgct caccacctta     180
caaaatttgt cgaacgacga gctgctgccc gttgcgcgtg cgtttagtca gttcctgaac     240
ctggccaaca ccgccgagca ataccacagc atttcgccga aggcgaagc tgccagcaac      300
ccggaagtga tcgcccgcac cctgcgtaaa ctgaaaaacc agccggaact gagcgaagac     360
accatcaaaa agcagtggat atcgctgtcg ctggaactgg tcctcacggc tcacccaacc     420
gaaattaccc gtcgtacact gatccacaaa atggtggaag tgaacgcctg tttaaaacag     480
ctcgataaca agatatcgc tgactacgaa cacaaccagc tgatgcgtcg cctgcgccag      540
ttgatcgccc agtcatggca taccgatgaa atccgtaagc tgcgtccaag cccggtagat     600
gaagccaaat ggggctttgc cgtagtggaa acagcctgt ggcaaggcgt accaaattac      660
ctgcgcgaac tgaacgaaca actggaagag aacctcggct acaaactgcc cgtcgaattt     720
gttccggtcc gttttacttc gtggatgggc ggcgaccgcg acggcaaccc gaacgtcact     780
gccgatatca cccgccacgt cctgctactc agccgctgga agccaccga tttgttcctg      840
aaagatattc aggtgctggt ttctgaactg tcgatggttg aagcgacccc tgaactgctg     900
gcgctggttg cgaagaagg tgccgcagaa ccgtatcgct atctgatgaa aaacctgcgt     960
tctcgcctga tggcgacaca ggcatggctg aagcgcgcc tgaaaggcga agaactgcca     1020
aaaccagaag gcctgctgac acaaaacgaa gaactgtggg aaccgctcta cgcttgctac    1080
cagtcacttc aggcgtgtgg catgggtatt atcgccaacg gcgatctgct cgacaccctg    1140
cgccgcgtga atgtttcgg cgtaccgctg gtccgtattg atatccgtca ggagagcacg    1200
cgtcataccg aagcgctggg cgagctgacc cgctacctcg gtatcggcga ctacgaaagc    1260
tggtcagagg ccgacaaaca ggcgttcctg atccgcgaac tgaactccaa acgtccgctt    1320
ctgccgcgca actggcaacc aagcgccgaa acgcgcgaag tgctcgatac ctgccaggtg    1380
attgccgaag caccgcaagg ctccattgcc gcctacgtga tctcgatggc gaaaacgccg    1440
tccgacgtac tggctgtcca cctgctgctg aaagaagcgg tatcgggtt tgcgatgccg    1500
gttgctccgc tgtttgaaac cctcgatgat ctgaacaacg ccaacgatgt catgacccag    1560
ctgctcaata ttgactggta tcgtggcctg attcagggca acagatggt gatgattggc    1620
tattccgact cagcaaaaga tgcgggagtg atggcagctt cctgggcgca atatcaggca    1680
caggatgcat taatcaaaac ctgcgaaaaa gcgggtattg agctgacgtt gttccacggt    1740
cgcggcggtt ccattggtcg cggcggcgca cctgctcatg cggcgctgct gtcacaaccg    1800
ccaggaagcc tgaaaggcgg cctgcgcgta accgaacagg cgagatgat ccgctttaaa    1860
tatggtctgc agaaatcac cgtcagcagc ctgtcgcttt ataccggggc gattctggaa    1920
gccaacctgc tgccaccgcc ggagccgaaa gagagctggc gtcgcattat ggatgaactg    1980
tcagtcatct cctgcgatgt ctaccgcggc tacgtacgtg aaaacaaaga ttttgtgcct    2040
tacttccgct ccgctacgcc ggaacaagaa ctgggcaaac tgccgttggg ttcacgtccg    2100
gcgaaacgtc gcccaaccgg cggcgtcgag tcactacgcg ccattccgtg gatcttcgcc    2160
tggacgcaaa accgtctgat gctccccgcc tggctgggtg caggtacggc gctgcaaaaa    2220
```

```
gtggtcgaag acggcaaaca gagcgagctg gaggctatgt gccgcgattg gccattcttc    2280
tcgacgcgtc tcggcatgct ggagatggtc ttcgccaaag cagacctgtg gctggcggaa    2340
tactatgacc aacgcctggt agacaaagca ctgtggccgt taggtaaaga gttacgcaac    2400
ctgcaagaag aagacatcaa agtggtgctg gcgattgcca acgattccca tctgatggcc    2460
gatctgccgt ggattgcaga gtctattcag ctacggaata tttacaccga cccgctgaac    2520
gtattgcagg ccgagttgct gcaccgctcc cgccaggcag aaaagaaagg ccaggaaccg    2580
gatcctcgcg tcgaacaagc gttaatggtc actattgccg ggattgcggc aggtatgcgt    2640
aataccggct aa                                                       2652

<210> SEQ ID NO 28
<211> LENGTH: 1191
<212> TYPE: DNA
<213> ORGANISM: Escherichia coli
<220> FEATURE:
<221> NAME/KEY: gene
<222> LOCATION: (1)..(1191)
<223> OTHER INFORMATION: aspartate aminotransferase

<400> SEQUENCE: 28
atgtttgaga acattaccgc cgctcctgcc gacccgattc tgggcctggc cgatctgttt      60
cgtgccgatg aacgtcccgg caaaattaac ctcgggattg gtgtctataa agatgagacg     120
ggcaaaaccc cggtactgac cagcgtgaaa aaggctgaac agtatctgct cgaaaatgaa     180
accaccaaaa attacctcgg cattgacggc atccctgaat ttggtcgctg cactcaggaa     240
ctgctgtttg gtaaaggtag cgccctgatc aatgacaaac gtgctcgcac ggcacagact     300
ccggggggca ctggcgcact acgcgtggct gccgatttcc tggcaaaaaa taccagcgtt     360
aagcgtgtgt gggtgagcaa cccaagctgg ccgaaccata gagcgtgtct taactctgca     420
ggtctggaag ttcgtgaata cgcttattat gatgcggaaa atcacactct tgacttcgat     480
gcactgatta acagcctgaa tgaagctcag gctggcgacg tagtgctgtt ccatggctgc     540
tgccataacc caaccggtat cgaccctacg ctggaacaat ggcaaacact ggcacaactc     600
tccgttgaga aaggctggtt accgctgttt gacttcgctt accagggttt tgcccgtggt     660
ctggaagaag atgctgaagg actgcgcgct ttcgcggcta tgcataaaga gctgattgtt     720
gccagttcct actctaaaaa ctttggcctg tacaacgagc gtgttggcgc ttgtactctg     780
gttgctgccg acagtgaaac cgttgatcgc gcattcagcc aaatgaaagc ggcgattcgc     840
gctaactact ctaacccacc agcacacggc gcttctgttg ttgccaccat cctgagcaac     900
gatgcgttac gtgcgatttg gaacaagagc tgactgata tgcgccagcg tattcagcgt     960
atgcgtcagt tgttcgtcaa tacgctgcag gaaaaaggcg caaaccgcga cttcagcttt    1020
atcatcaaac agaacggcat gttctccttc agtggcctga caaaagaaca agtgctgcgt    1080
ctgcgcgaag agtttggcgt atatgcggtt gcttctggtc gcgtaaatgt ggccgggatg    1140
acaccagata acatggctcc gctgtgcgaa gcgattgtgg cagtgctgta a             1191

<210> SEQ ID NO 29
<211> LENGTH: 1104
<212> TYPE: DNA
<213> ORGANISM: Escherichia coli
<220> FEATURE:
<221> NAME/KEY: gene
<222> LOCATION: (1)..(1104)
<223> OTHER INFORMATION: aspartate-semialdehyde dehydrogenase

<400> SEQUENCE: 29
```

```
atgaaaaatg ttggtttat cggctggcgc ggtatggtcg gctccgttct catgcaacgc    60
atggttgaag agcgcgactt cgacgccatt cgccctgtct tcttttctac ttctcagctt   120
ggccaggctg cgccgtcttt tggcggaacc actggcacac ttcaggatgc ctttgatctg   180
gaggcgctaa aggccctcga tatcattgtg acctgtcagg gcggcgatta taccaacgaa   240
atctatccaa agcttcgtga agcggatgg caaggttact ggattgacgc agcatcgtct    300
ctgcgcatga aagatgacgc catcatcatt cttgaccccg tcaatcagga cgtcattacc   360
gacggattaa ataatggcat caggactttt gttggcggta actgtaccgt aagcctgatg   420
ttgatgtcgt tgggtggttt attcgccaat gatcttgttg attgggtgtc cgttgcaacc   480
taccaggccg cttccggcgg tggtgcgcga catatgcgtg agttattaac ccagatgggc   540
catctgtatg gccatgtggc agatgaactc gcgaccccgt cctctgctat tctcgatatc   600
gaacgcaaag tcacaacctt aacccgtagc ggtgagctgc cggtggataa ctttggcgtg   660
ccgctggcgg gtagcctgat tccgtggatc gacaaacagc tcgataacgg tcagagccgc   720
gaagagtgga agggcaggc ggaaaccaac aagatcctca acacatcttc cgtaattccg    780
gtagatggtt tatgtgtgcg tgtcggggca ttgcgctgcc acagccaggc attcactatt   840
aaattgaaaa aagatgtgtc tattccgacc gtggaagaac tgctggctgc gcacaatccg   900
tgggcgaaag tcgttccgaa cgatcgggaa atcactatgc gtgagctaac cccagctgcc   960
gttaccggca cgctgaccac gccggtaggc cgcctgcgta agctgaatat gggaccagag  1020
ttcctgtcag cctttaccgt gggcgaccag ctgctgtggg gggccgcgga gccgctgcgt  1080
cggatgcttc gtcaactggc gtaa                                         1104
```

<210> SEQ ID NO 30
<211> LENGTH: 70
<212> TYPE: DNA
<213> ORGANISM: Artificial Sequence
<220> FEATURE:
<223> OTHER INFORMATION: Primer

<400> SEQUENCE: 30

```
ttactctggt gcctgacatt tcaccgacaa agcccaggga acttcatcac gtgtaggctg    60
gagctgcttc                                                          70
```

<210> SEQ ID NO 31
<211> LENGTH: 70
<212> TYPE: DNA
<213> ORGANISM: Artificial Sequence
<220> FEATURE:
<223> OTHER INFORMATION: Primer

<400> SEQUENCE: 31

```
ttaccccttg tttgcagccc ggaagccatt ttccaggtcg gcaattaaat catatgaata    60
tcctccttag                                                          70
```

<210> SEQ ID NO 32
<211> LENGTH: 70
<212> TYPE: DNA
<213> ORGANISM: Artificial Sequence
<220> FEATURE:
<223> OTHER INFORMATION: Primer

<400> SEQUENCE: 32

```
aaagaatatg ccgatcggtt cgggcttagg ctccagtgcc tgttcggtgg gtgtaggctg    60
```

```
gagctgcttc                                                              70

<210> SEQ ID NO 33
<211> LENGTH: 70
<212> TYPE: DNA
<213> ORGANISM: Artificial Sequence
<220> FEATURE:
<223> OTHER INFORMATION: Primer

<400> SEQUENCE: 33
agacaaccga catcgctttc aacattggcg accggagccg ggaaggcaaa catatgaata     60
tcctccttag                                                              70

<210> SEQ ID NO 34
<211> LENGTH: 29
<212> TYPE: DNA
<213> ORGANISM: Artificial Sequence
<220> FEATURE:
<223> OTHER INFORMATION: Primer

<400> SEQUENCE: 34
aattgatatc atgccgattc gtgtgccgg                                         29

<210> SEQ ID NO 35
<211> LENGTH: 34
<212> TYPE: DNA
<213> ORGANISM: Artificial Sequence
<220> FEATURE:
<223> OTHER INFORMATION: Primer

<400> SEQUENCE: 35
aattaagctt ttaatccagc gttggattca tgtg                                   34

<210> SEQ ID NO 36
<211> LENGTH: 44
<212> TYPE: DNA
<213> ORGANISM: Artificial Sequence
<220> FEATURE:
<223> OTHER INFORMATION: Primer

<400> SEQUENCE: 36
ttgtaactgg tgcgccgctg gaactggtgg ggtttaatga tgtc                        44

<210> SEQ ID NO 37
<211> LENGTH: 44
<212> TYPE: DNA
<213> ORGANISM: Artificial Sequence
<220> FEATURE:
<223> OTHER INFORMATION: Primer

<400> SEQUENCE: 37
gacatcatta aaccccacca gttccagcgg cgcaccagtt acaa                        44

<210> SEQ ID NO 38
<211> LENGTH: 44
<212> TYPE: DNA
<213> ORGANISM: Artificial Sequence
<220> FEATURE:
<223> OTHER INFORMATION: Primer

<400> SEQUENCE: 38
tgtaactggt gcgccgctgg aacatgtggg gtttaatgat gtcg                        44

<210> SEQ ID NO 39
<211> LENGTH: 44
```

<212> TYPE: DNA
<213> ORGANISM: Artificial Sequence
<220> FEATURE:
<223> OTHER INFORMATION: Primer

<400> SEQUENCE: 39
cgacatcatt aaaccccaca tgttccagcg gcgcaccagt taca                44

<210> SEQ ID NO 40
<211> LENGTH: 42
<212> TYPE: DNA
<213> ORGANISM: Artificial Sequence
<220> FEATURE:
<223> OTHER INFORMATION: Primer

<400> SEQUENCE: 40
tttccgaaac gtacctcagc aggtgtaggc tggagctgct tc                  42

<210> SEQ ID NO 41
<211> LENGTH: 43
<212> TYPE: DNA
<213> ORGANISM: Artificial Sequence
<220> FEATURE:
<223> OTHER INFORMATION: Primer

<400> SEQUENCE: 41
gaataaaatt tattcacctg ctgcatatga atatcctcct tag                 43

<210> SEQ ID NO 42
<211> LENGTH: 29
<212> TYPE: DNA
<213> ORGANISM: Artificial Sequence
<220> FEATURE:
<223> OTHER INFORMATION: Primer

<400> SEQUENCE: 42
aattgatatc atgccgattc gtgtgccgg                                 29

<210> SEQ ID NO 43
<211> LENGTH: 27
<212> TYPE: DNA
<213> ORGANISM: Artificial Sequence
<220> FEATURE:
<223> OTHER INFORMATION: Primer

<400> SEQUENCE: 43
aattaagcct gctgaggtac gtttcgg                                   27

<210> SEQ ID NO 44
<211> LENGTH: 23
<212> TYPE: DNA
<213> ORGANISM: Artificial Sequence
<220> FEATURE:
<223> OTHER INFORMATION: Primer

<400> SEQUENCE: 44
cagcaggtga ataaatttta ttc                                       23

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
cgcgaatgga agctgtttcc                                          20

<210> SEQ ID NO 46
<211> LENGTH: 31
<212> TYPE: DNA
<213> ORGANISM: Artificial Sequence
<220> FEATURE:
<223> OTHER INFORMATION: Primer

<400> SEQUENCE: 46
gccggaattc tgtcggatgc gatacttgcg c                             31

<210> SEQ ID NO 47
<211> LENGTH: 30
<212> TYPE: DNA
<213> ORGANISM: Artificial Sequence
<220> FEATURE:
<223> OTHER INFORMATION: Primer

<400> SEQUENCE: 47
gaaggagctc agaaaaccct cgcgcaaaag                               30

<210> SEQ ID NO 48
<211> LENGTH: 31
<212> TYPE: DNA
<213> ORGANISM: Artificial Sequence
<220> FEATURE:
<223> OTHER INFORMATION: Primer

<400> SEQUENCE: 48
aaaaaaaaaa aaaaaaaaaa aaaaaaaaaa a                             31

<210> SEQ ID NO 49
<211> LENGTH: 30
<212> TYPE: DNA
<213> ORGANISM: Artificial Sequence
<220> FEATURE:
<223> OTHER INFORMATION: Primer

<400> SEQUENCE: 49
gaagggtacc agaaaaccct cgcgcaaaag                               30

<210> SEQ ID NO 50
<211> LENGTH: 30
<212> TYPE: DNA
<213> ORGANISM: Artificial Sequence
<220> FEATURE:
<223> OTHER INFORMATION: Primer

<400> SEQUENCE: 50
tccgagctca taagcgtagc gcatcaggca                               30

<210> SEQ ID NO 51
<211> LENGTH: 30
<212> TYPE: DNA
<213> ORGANISM: Artificial Sequence
<220> FEATURE:
<223> OTHER INFORMATION: Primer

<400> SEQUENCE: 51
tccgagctcg tccacctatg ttgactacat                               30

<210> SEQ ID NO 52
<211> LENGTH: 27
<212> TYPE: DNA
<213> ORGANISM: Artificial Sequence
<220> FEATURE:
<223> OTHER INFORMATION: Primer

<400> SEQUENCE: 52
ccggaattcc caggagagca ataagca                                          27

<210> SEQ ID NO 53
<211> LENGTH: 28
<212> TYPE: DNA
<213> ORGANISM: Artificial Sequence
<220> FEATURE:
<223> OTHER INFORMATION: Primer

<400> SEQUENCE: 53
ctagtctaga tgctctattt aactcccg                                         28

<210> SEQ ID NO 54
<211> LENGTH: 28
<212> TYPE: DNA
<213> ORGANISM: Artificial Sequence
<220> FEATURE:
<223> OTHER INFORMATION: Primer

<400> SEQUENCE: 54
ctagtctaga ccaggagagc aataagca                                         28

<210> SEQ ID NO 55
<211> LENGTH: 27
<212> TYPE: DNA
<213> ORGANISM: Artificial Sequence
<220> FEATURE:
<223> OTHER INFORMATION: Primer

<400> SEQUENCE: 55
ccggaattct gctctattta actcccg                                          27

<210> SEQ ID NO 56
<211> LENGTH: 70
<212> TYPE: DNA
<213> ORGANISM: Artificial Sequence
<220> FEATURE:
<223> OTHER INFORMATION: Primer

<400> SEQUENCE: 56
aggcgctaag gagaccttaa atggctgata caaaagcaaa actcaccctc tgtaggctgg      60
agctgcttcg                                                             70

<210> SEQ ID NO 57
<211> LENGTH: 70
<212> TYPE: DNA
<213> ORGANISM: Artificial Sequence
<220> FEATURE:
<223> OTHER INFORMATION: Primer

<400> SEQUENCE: 57
gggttaaaat atttacaact tagcaatcaa ccattaacgc ttgatatcgc atgggaatta      60
gccatggtcc                                                             70

<210> SEQ ID NO 58
<211> LENGTH: 22
<212> TYPE: DNA
<213> ORGANISM: Artificial Sequence
<220> FEATURE:
<223> OTHER INFORMATION: Primer

<400> SEQUENCE: 58
cctttctata actgcgcgtc at                                              22

<210> SEQ ID NO 59
<211> LENGTH: 21
<212> TYPE: DNA
<213> ORGANISM: Artificial Sequence
<220> FEATURE:
<223> OTHER INFORMATION: Primer

<400> SEQUENCE: 59
aggggtatag ctacgccaga a                                               21

<210> SEQ ID NO 60
<211> LENGTH: 20
<212> TYPE: DNA
<213> ORGANISM: Artificial Sequence
<220> FEATURE:
<223> OTHER INFORMATION: Primer

<400> SEQUENCE: 60
gaaggcaaat ttaagttccg                                                 20

<210> SEQ ID NO 61
<211> LENGTH: 40
<212> TYPE: DNA
<213> ORGANISM: Artificial Sequence
<220> FEATURE:
<223> OTHER INFORMATION: Primer

<400> SEQUENCE: 61
cgaagcagct ccagcctaca ggtatagata gacgtcattt                           40

<210> SEQ ID NO 62
<211> LENGTH: 42
<212> TYPE: DNA
<213> ORGANISM: Artificial Sequence
<220> FEATURE:
<223> OTHER INFORMATION: Primer

<400> SEQUENCE: 62
cggcgcgctg gcggcgttcg cgcacgactc gctggatgtt aa                        42

<210> SEQ ID NO 63
<211> LENGTH: 42
<212> TYPE: DNA
<213> ORGANISM: Artificial Sequence
<220> FEATURE:
<223> OTHER INFORMATION: Primer

<400> SEQUENCE: 63
ttaacatcca gcgagtcgtg cgcgaacgcc gccagcgcgc cg                        42

<210> SEQ ID NO 64
<211> LENGTH: 42
<212> TYPE: DNA
<213> ORGANISM: Artificial Sequence
<220> FEATURE:
<223> OTHER INFORMATION: Primer

<400> SEQUENCE: 64
cgcgttccgc ctgctgtcgg cgatgccgac catggccgcg at                        42

<210> SEQ ID NO 65
<211> LENGTH: 42

```
<212> TYPE: DNA
<213> ORGANISM: Artificial Sequence
<220> FEATURE:
<223> OTHER INFORMATION: Primer

<400> SEQUENCE: 65
atcgcggcca tggtcggcat cgccgacagc aggcggaacg cg                          42

<210> SEQ ID NO 66
<211> LENGTH: 40
<212> TYPE: DNA
<213> ORGANISM: Artificial Sequence
<220> FEATURE:
<223> OTHER INFORMATION: Primer

<400> SEQUENCE: 66
tcctgaatat gatgttctcc gcgccgtgcg aaccgtatga                             40

<210> SEQ ID NO 67
<211> LENGTH: 40
<212> TYPE: DNA
<213> ORGANISM: Artificial Sequence
<220> FEATURE:
<223> OTHER INFORMATION: Primer

<400> SEQUENCE: 67
tcatacggtt cgcacggcgc ggagaacatc atattcagga                             40

<210> SEQ ID NO 68
<211> LENGTH: 40
<212> TYPE: DNA
<213> ORGANISM: Artificial Sequence
<220> FEATURE:
<223> OTHER INFORMATION: Primer

<400> SEQUENCE: 68
aaatgacgtc tatctatacc tgtaggctgg agctgcttcg                             40

<210> SEQ ID NO 69
<211> LENGTH: 76
<212> TYPE: DNA
<213> ORGANISM: Artificial Sequence
<220> FEATURE:
<223> OTHER INFORMATION: Primer

<400> SEQUENCE: 69
gcaaaactaa attattggta tcatgaattt gttgtatgat gaataaaata tagggatgg        60 gaattagcca tggtcc                                                      76

<210> SEQ ID NO 70
<211> LENGTH: 67
<212> TYPE: DNA
<213> ORGANISM: Artificial Sequence
<220> FEATURE:
<223> OTHER INFORMATION: Primer

<400> SEQUENCE: 70
ccatggagga ggaattaacc atgcagtggt ggtggtggtg gtgcgataac agctgtatcc       60
ccgttga                                                                67

<210> SEQ ID NO 71
<211> LENGTH: 67
<212> TYPE: DNA
<213> ORGANISM: Artificial Sequence
<220> FEATURE:
```

| | |
|---|---|
| <223> OTHER INFORMATION: Primer | |
| <400> SEQUENCE: 71 | |
| aagcttagga ggaattaacc atgcagtggt ggtggtggtg gtgcgatgca aatttaagtt | 60 |
| ccggcag | 67 |

MICROORGANISM PRODUCING O-ACETYL HOMOSERINE AND THE METHOD OF PRODUCING O-ACETYL HOMOSERINE USING THE SAME

CROSS-REFERENCE TO RELATED APPLICATIONS

This application is a U.S. national phase application of International PCT Patent Application No. PCT/KR2015/006307, which was filed on Jun. 22, 2015, which claims priority to Korean Patent Application Nos. 10-2014-0076779, filed Jun. 23, 2014. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_040_01US_SeqList_ST25.txt. The text file is 87 KB, was created on Dec. 21,2015, and is being submitted electronically via EFS-Web.

TECHNICAL FIELD

The present invention relates to a microorganism of *Escherichia* sp. producing O-acetyl homoserine, and a method of producing O-acetyl homoserine in high yield using the microorganism.

BACKGROUND ART

O-Acetyl homoserine acts as a precursor of methionine, which is one of the essential amino acids in the body. Methionine has been widely used a component of medical infusion solutions and raw materials for medicinal products as well as an animal feed and food additive.

Methionine can be biologically or chemically synthesized. Recently, a two-step process, in which an L-methionine precursor produced by fermentation is converted to L-methionine by an enzyme reaction, was disclosed (International Publication No. WO 2008/013432). In the above two-step process, O-succinyl homoserine and O-acetyl homoserine may be used as the methionine precursor, and it is important that O-acetyl homoserine be produced in high yield for large-scale cost-effective production of methionine.

DISCLOSURE

Technical Problem

The present inventors, while endeavoring to improve the production of O-acetyl homoserine, discovered that the reduction of the expression or activity of citrate synthase protein can significantly increase the production capability of O-acetyl homoserine, thereby completing the present invention.

Technical Solution

An object of the present invention is to provide an O-acetyl homoserine-producing microorganism with improved O-acetyl homoserine production capability.

Another object of the present invention is to provide a method for producing O-acetyl homoserine using the microorganism.

Advantageous Effects

The use of the microorganism with O-acetyl homoserine production capability according to the present invention can produce O-acetyl homoserine in a higher yield and in a more environmentally friendly manner than chemical synthesis. Additionally, the thus produced O-acetyl homoserine can be used as a precursor for the synthesis of methionine and acetic acid by O-acetyl homoserine sulfhydrylase, thereby enabling bioconversion of L-methionine, and the thus converted L-methionine can be widely used in the production of foods or food additives for humans as well as animal feeds or animal feed additives.

DESCRIPTION OF DRAWINGS

FIG. 1 is an expression cassette design for the construction of a microorganism with an attenuated activity of citrate synthase.

FIG. 2 is a restriction map of pBAD24-citrate synthase antisense RNA (asRNA) vector.

BEST MODE

In an aspect, the present invention provides a microorganism of *Escherichia* sp. producing O-acetyl homoserine, in which the activity of endogenous citrate synthase protein is attenuated or inactivated.

As used herein, the term "O-acetyl homoserine", being a specific intermediate material in a methionine biosynthesis pathway of a microorganism, refers to an acetyl-derivative of L-homoserine. O-acetyl homoserine can be produced by an enzyme activity of transferring an acetyl group from acetyl-CoA to homoserine using homoserine and acetyl-CoA as substrates.

As used herein, the term "a microorganism producing O-acetyl homoserine" includes a microorganism, which, being a eukaryotic or prokaryotic microorganism producing O-acetyl homoserine within a living organism, is provided with O-acetyl homoserine-producing capability to its parent microorganism without O-acetyl homoserine-producing capability, or a microorganism which is endogenously provided with the O-acetyl homoserine-producing capability.

O-Acetyl homoserine-producing capability may be provided or promoted by improvement of species. The microorganisms having the O-acetyl homoserine-producing capability may include microorganism belonging to *Escherichia* sp., *Erwinia* sp., *Serratia* sp., *Providencia* sp., *Corynebacteria* sp., *Pseudomonas* sp., *Leptospira* sp., *Salmonella* sp., *Brevibacteria* sp., *Hypomononas* sp., *Chromobacterium* sp., and *Norcardia* sp., or fungi, or yeasts; specifically, microorganism belonging to *Escherichia* sp., Corynebacteria sp., *Leptospira* sp., and yeasts; and more specifically, microorganism belonging to *Escherichia* sp., as a specific example, *Escherichia coli*. The microorganisms having the O-acetyl homoserine-producing capability may be microorganisms producing L-lysine, L-threonine, L-isoleucine, or L-methionine, or derivatives thereof, but are not limited thereto.

As used herein, the term "citrate synthase (E.C. 2.3.3.1)" refers to an enzyme in the first step of the TCA cycle that mediates the reaction between oxaloacetate and acetyl-CoA. Specifically, citrate synthase mediates the condensation reaction between an acetate residue having two carbon atoms, which is in acetyl-CoA, and oxaloacetate having four carbon atoms, thereby generating a citrate having six carbon atoms. In *Escherichia coli*, citrate synthase is designated GltA, and citrate synthase and GltA are interchangeably used in the present invention.

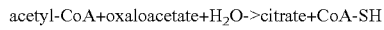

acetyl-CoA+oxaloacetate+H₂O->citrate+CoA-SH

Specifically, citrate synthase may be one derived from *Escherichia* sp., and more specifically, GltA derived from *Escherichia coli*. Citrate synthase may be a protein comprising an amino acid sequence represented by SEQ ID NO: 4 or those having a homology of 70% or higher with amino acid sequence of SEQ ID NO: 4, specifically 80% or higher, or more specifically, 90% or higher. Additionally, as a sequence having a homology, if the amino acid sequence is one having the same or corresponding activity of citrate synthase with that of SEQ ID NO: 4, it is obvious that amino acid sequences with a deletion, a modification, a substitution, or an addition, in part of the sequences should also be included in the scope of the present invention. Additionally, based on the genetic code degeneracy, polynucleotide sequences encoding the same amino acid sequence and variants thereof should also be included in the scope of the present invention.

As used herein, the term "endogenous" activity refers to a natural state of a protein in a microorganism or an activity state of the corresponding protein provided in the microorganism before modification.

The "the attenuation or inactivation of a protein activity compared to its endogenous activity" refers to a reduction or elimination of the protein activity when compared with that possessed in its natural state. The attenuation is a concept referring to a case when the activity of a protein is reduced compared with that originally possessed by the microorganism due to a modification in the protein-encoding gene, a case when the level of overall protein expression is lower than that of the natural type strain of the microorganism, or a combination thereof, but is not limited thereto. The inactivation includes a case when the gene encoding the protein is not expressed at all compared to that of the natural type strain, and a case when the gene is expressed but exhibits no activity.

The attenuation or inactivation of a protein activity may be achieved by various methods well known in the art. Examples of the methods may include a method of replacing the gene encoding the protein on the chromosome with a gene modified so that the enzyme activity can be reduced including the case when the protein activity is removed; a method of introducing a modification on the expression-regulating sequence of the gene encoding the protein on the chromosome; a method of replacing the expression-regulating sequence of the gene encoding the protein with a sequence having a weak activity or no activity; a method of deleting a part of or the entire gene encoding the protein on the chromosome; a method of introducing an antisense oligonucleotide (e.g., antisense RNA), which inhibits the translation from the mRNA into a protein via a complementary binding to the transcript of the gene on the chromosome; a method of making the attachment of ribosome impossible by forming a secondary structure by artificially adding a Shine-Dalgarno (SD) sequence and its complementary sequence on the front end of the SD sequence of the gene encoding the protein; a method of reverse transcription engineering (RTE), which adds a promoter so as to be reversely transcribed on the 3' terminus of the open reading frame (ORF) of the corresponding sequence, etc., and also include a combination thereof, but are not limited thereto.

Specifically, the method of deleting a part of or the entire gene encoding a protein may be performed by replacing the polynucleotide, encoding the endogenous target protein within the chromosome via a vector for inserting chromosome into a microorganism, with a polynucleotide or a marker where part of the polynucleotide sequence is deleted. For example, a method of gene deletion via homologous recombination may be used, but is not limited thereto. Additionally, as used herein the term "part", although it may vary depending on the kinds of polynucleotide, may specifically refer to 1 nucleotide to 300 nucleotides, more specifically 1 nucleotide to 100 nucleotides, and even more specifically 1 nucleotide to 50 nucleotides, but is not limited thereto.

Additionally, the method of modifying the expression regulation sequence may be performed by inducing a variation on the expression regulation sequence of the polynucleotide sequence via deletion, insertion, conservative substitution, non-conservative substitution, or a combination thereof so as to further attenuate the activity of the expression regulation sequence; or by replacing the polynucleotide sequence with a polynucleotide sequence with a weaker activity. The polynucleotide sequence may include a promoter, an operator sequence, a sequence encoding a ribosome-binding domain, and a sequence for regulating termination of transcription and translation, but is not limited thereto.

Additionally, the method of modifying the gene sequence on the chromosome may be performed by inducing a variation in the sequence via deletion, insertion, conservative substitution, non-conservative substitution, or a combination thereof so as to further attenuate the activity of the expression regulation sequence; or by replacing the sequence with a gene sequence improved to have a weaker activity or a gene sequence improved to have no activity, but is not limited thereto.

Specifically, for the attenuation of the activity of citrate synthase protein, part of an amino acid(s) in the amino acid sequence of the citrate synthase protein may be substituted with other amino acid(s). More specifically, a citrate synthase having an amino acid sequence, in which the $145^{th}$ amino acid or the $167^{th}$ amino acid in the amino acid sequence of the citrate synthase protein is substituted from tyrosine (Y) or lysine (K) to other amino acid(s) may be included. Even more specifically, the citrate synthase may be one having a gene sequence encoding a modified polypeptide, in which the $145^{th}$ amino acid in the amino acid sequence of the citrate synthase protein is substituted from tyrosine (Y) to alanine (A), and the $167^{th}$ amino acid is substituted from lysine (K) to alanine (A). In particular, the amino acid residue number was determined in sequential order after setting the amino acid positioned next to the methionine, which is encoded by the initiation codon, as the $1^{st}$ amino acid. The polypeptide may respectively have an amino acid sequence represented by SEQ ID NO: 1 or 2. Additionally, if the activity of the citrate synthase is weaker than that of a wild-type, the citrate synthase may include amino acid sequences having a homology of 80% or higher with the amino acid sequence of SEQ ID NO: 1 or 2, specifically 90% or higher, more specifically 95% or higher, and even more specifically 97% or higher. As a sequence having a homology, if the amino acid sequence is one which has substantially the same or corresponding biological activity of a protein of SEQ ID NO: 1 or 2, it is obvious that amino acid sequences with a deletion, a modification, a substitution, or an addition in part of the sequences should also be included in the scope of the present invention.

As used herein, the term "homology" refers to a percentage in identity between two polynucleotides or polypeptide moieties. The homology between sequences from a moiety to another moiety may be determined by a technology known in the art. For example, the homology may be determined by directly arranging the sequence information between two different polynucleotide molecules or two different polypeptides using a computer program arranging and easily obtaining the sequence information. The computer program may include BLAST (NCBI), CLC Main Workbench (CLC bio), MegAlignTM (DNASTAR Inc), etc. Additionally, the homology between polynucleotides may be determined by hybridizing the polynucleotides under the condition of forming a stable double strand between homologous regions, decomposing with a single-strand-specific nuclease, and determining the decomposed fragments.

As used herein, the term "homology" refers to a relationship between proteins having "common evolutionary origin" including homologous proteins derived from superfamily proteins in all grammatical forms or with spelling variations, and those derived from different species. These proteins (and the genes encoding the same) have sequence homologies reflected by high levels of sequence similarities. However, the term "homology", for its general use and the use in the present invention, would refer to a sequence similarity when modified by an adjective such as "very high", instead of referring to common evolutionary origin.

In an exemplary embodiment of the present invention, the microorganism may be one in which the activity of cystathionine gamma synthase (EC 2.5.1.48), homoserine kinase (EC 2.7.1.39), or the activities of both are weaker than their endogenous activities, or inactivated.

As used herein, the term "cystathionine gamma synthase" refers to an enzyme which can synthesize cystathionine by a chemical reaction described below, using O-succinyl homoserine and L-cysteine as substrates. In the present invention, the cystathionine gamma synthase from *E. coli*, is designated as "MetB".

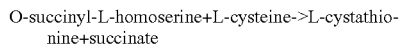
O-succinyl-L-homoserine+L-cysteine->L-cystathionine+succinate

Specifically, the cystathionine gamma synthase from *E. coli*, although not particularly limited thereto, may be a protein comprising an amino acid sequence represented by SEQ ID NO: 9 or those having a homology of 70% or higher with the amino acid sequence of SEQ ID NO: 9, specifically 80% or higher, and more specifically 90% or higher. Additionally, as a sequence having a homology, if the amino acid sequence is one having the same or corresponding activity of homoserine kinase with the amino acid sequence of SEQ ID NO: 9, it is obvious that amino acid sequences with a deletion, a modification, a substitution, or an addition in part of the sequences should also be included in the scope of the present invention. Additionally, based on the genetic code degeneracy, polynucleotide sequences encoding the same amino acid sequence and variants thereof should also be included in the scope of the present invention.

The method for attenuation and inactivation of the cystathionine gamma synthase activity may be performed according to the method described above.

As used herein, the term "homoserine kinase" refers to an enzyme causing the phosphorylation of homoserine, which performs the chemical reaction described below. In the present invention, the homoserine kinase from *E. coli*, is designated as "ThrB".

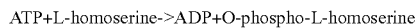
ATP+L-homoserine->ADP+O-phospho-L-homoserine

Specifically, homoserine kinase from *Escherichia* sp., although not particularly limited thereto, may be a protein comprising an amino acid sequence represented by SEQ ID NO: 11 or those having a homology of 70% or higher with the amino sequence of SEQ ID NO: 11, specifically 80% or higher, or more specifically, 90% or higher. Additionally, as a sequence having a homology, if the amino acid sequence is one having the same or corresponding activity of homoserine kinase with the amino sequence of SEQ ID NO: 11, it is obvious that amino acid sequences with a deletion, a modification, a substitution, or an addition in part of the sequences should also be included in the scope of the present invention. Additionally, based on the genetic code degeneracy, polynucleotide sequences encoding the same amino acid sequence and variants thereof should also be included in the scope of the present invention.

The method for attenuation and inactivation of the homoserine kinase activity may be performed according to the method described above.

In a specific aspect of the present invention, the microorganism may be one, in which the activity of homoserine O-acetyltransferase is further introduced or enhanced, or the endogenous homoserine O-succinyltransferase is further modified to have the activity of homoserine O-acetyltransferase.

As used herein, the term "homoserine O-acetyltransferase (EC 2.3.1.31)" refers to an enzyme having an activity of transferring an acetyl group from acetyl-CoA to homoserine.

Specifically, the microorganism according to the present invention may be introduced with the activity of homoserine O-acetyltransferase. The homoserine O-acetyltransferase may be derived from various microorganism species, for example, from a microorganism selected from *Corynebacteria* sp., *Leptospira* sp., *Deinococcus* sp., *Deinococcus* sp., *Pseudomonas* sp., and *Mycobacterium* sp. Specifically, the homoserine O-acetyltransferase may be those which include the amino acid sequences represented by SEQ ID NO: 13 (*Leptospira meyeri*), SEQ ID NO: 14 (*Corynebacterium glutamicum*), or SEQ ID NO: 15 (*Deinococcus radiodurans*), but is not limited thereto. Additionally, the homoserine O-acetyltransferase may be a protein comprising the above amino acid sequences or those having a homology of 70% or higher with the above amino acid sequences, specifically 80% or higher, or more specifically, 90% or higher. Additionally, based on the genetic code degeneracy, polynucleotide sequences encoding the same amino acid sequence and variants thereof should also be included in the scope of the present invention.

Examples of the homoserine O-acetyltransferase to be used in the present invention are disclosed in Korean Patent Application Publication No. 10-2011-0023703 and European Patent Application Publication No. EP 2290051, and the entire specifications of these patent documents may be included as references in the present invention.

Additionally, the protein, in which the endogenous homoserine O-succinyltransferase (EC 2.3.1.46) is modified to have the activity of homoserine O-acetyltransferase, refers to a polypeptide, in which the substrate specificity of the polypeptide having the homoserine O-succinyltransferase activity is changed from succinyl-CoA to acetyl-CoA. Additionally, the modified protein, although not particularly limited thereto, may be a polypeptide having homoserine O-acetyltransferase activity, unlike its wild-type, by replacing part of the amino acid sequence of the polypeptide having homoserine O-succinyltransferase activity.

Examples of the homoserine O-succinyltransferase may be a polypeptide from *Enterobacteria* sp., *Salmonella* sp., Pseudomonas sp., Bacillus sp., or Escherichia sp., specifically, a polypeptide from Escherichia sp. having the homoserine O-succinyltransferase activity, for example, a polypeptide having homoserine O-succinyltransferase activity from E. coli. More specifically, the homoserine O-succinyltransferase from E. coli may have the amino acid sequence represented SEQ ID NO: 16, but is not limited thereto. The homoserine O-succinyltransferase from E. coli is designated as "MetA".

The modified homoserine O-succinyltransferase may be a variant polypeptide, in which the 111$^{th}$ amino acid of the polypeptide represented by SEQ ID NO: 16 or polypeptides having a homology of 95% or above with the polynucleotide sequence of SEQ ID NO: 16 is substituted with glutamic acid, and additionally, the 112$^{nd}$ amino acid is substituted with threonine or histidine. Specifically, the variant polypeptide may be a polypeptide having the amino acid sequence of any of SEQ ID NOS: 17 to 19. Additionally, the variant polypeptide may be a protein comprising an amino acid sequence having a homology of 70% or higher with the above amino acid sequence, specifically 80% or higher, or more specifically 90% or higher. Additionally, based on the genetic code degeneracy, polynucleotide sequences encoding the same amino acid sequence and variants thereof should also be included in the scope of the present invention. The information on the modified homoserine O-succinyltransferase can be obtained from Korean Patent Application Publication No. 10-2012-0070531 or International Publication No. WO2012/087039, and the entire specifications of these patent documents are included as references to the present invention.

As used herein, the term "introduction or enhancement of activity" refers to providing the activity of a particular protein to a microorganism which does not possess the protein; or enhancement of the intracellular activity of the protein in the microorganism which possesses the protein, and the like, and refers to the increase of the intracellular activity of the protein compared to the endogenous activity of the protein.

As used herein, the term "introduction or enhancement of protein activity" refers to not only the drawing of a higher effect than the original function due to the increase in the activity of the protein itself, but also the increase in the activity of the protein due to the increase in endogenous gene activity, endogenous gene amplification by the internal or external factors, the increase in copy number, gene introduction from outside, increase in enzyme activity due to the substitution, modification, or mutation, etc., but is not limited thereto.

In the above, the increase in gene copy number, although not particularly limited thereto, may be performed in a state operably connected to a vector, or by being inserted into the chromosome within a host cell. Specifically, the method may be executed by introducing a vector, which a polynucleotide encoding the protein of the present invention is operably connected to and can be replicated and function irrespective of a host, into a cell of the host; or introducing a vector, to which the polynucleotide is operably connected, inserting the polynucleotide into the chromosome of the host cell, into the host cell, thereby increasing the number of gene copies within the chromosome of the host cell.

The vector is a DNA construct including the polynucleotide sequence of the polynucleotide encoding the target protein, which is operably connected to a suitable regulation sequence so that the target protein can be expressed in an appropriate host, wherein the regulation sequence includes a promoter initiating transcription, a random operator sequence for regulation of the transcription, a sequence encoding a suitable mRNA ribosome-binding domain, and a sequence for regulation of transcription and translation. The vector, after being transformed into a suitable host cell, may be replicated or function irrespective of the host genome, or may be integrated into the host genome itself.

The vector used in the present invention may not be specifically limited as long as the vector is replicable in the host cell, and any vector known in the art may be used. Examples of the vector may include natural or recombinant plasmids, cosmids, viruses, and bacteriophages. For example, as a phage vector or cosmid vector, pWE15, M13, λMBL3, λMBL4, λIXII, λASHII, λAPII, λt10, λt11, Charon4A, Charon21A, etc., may be used; and as a plasmid vector, pBR-based, pUC-based, pBluescriptII-based, pGEM-based, pTZ-based, pCL-based, pET-based, etc., may be used. Specifically, pDZ, pACYC177, pACYC184, pCL, pECCG117, pUC19, pBR322, pMW118, pCC1BAC vectors, etc., may be used.

Additionally, a polynucleotide encoding an endogenous target protein may be substituted with a modified polynucleotide using a vector for inserting into the chromosome of a microorganism. The insertion of the polynucleotide into the chromosome may be performed using a known method in the art, for example, by homologous recombination. Since the vector of the present invention can be inserted into the chromosome via homologous recombination, a selection marker for confirmation of the insertion into the chromosome may be additionally included. The selection marker is used for selection of a transformed cell, i.e., in order to confirm whether the target polynucleotide has been inserted, and markers providing selectable phenotypes such as drug resistance, nutrient requirement, resistance to cytotoxic agents, and expression of surface proteins may be used, but are not limited thereto. Under the circumstances where selective agents are treated, only the cells expressing the selection markers can survive or express other phenotypic traits, and thus the transformed cells can be easily selected.

As used herein, the term "transformation" refers to a process of introducing a vector including a polynucleotide encoding a target protein into a host cell thereby enabling the expression of the polynucleotide encoded by the protein in the host cell. For the transformed polynucleotide, it does not matter whether it is inserted into the chromosome of a host cell and located therein and located outside the chromosome, as long as it can be expressed in the host cell. Additionally, the polynucleotide includes DNA and RNA which encode the target protein. The polynucleotide may be inserted in any form insofar as it can be introduced into a host cell and expressed therein. For example, the polynucleotide may be introduced into a host cell in the form of an expression cassette, which is a genetic construct including all essential elements required for self-expression. The expression cassette may conventionally include a promoter operably connected to the polynucleotide, a transcription termination signal, a ribosome-binding domain, and a translation termination signal, and may be in the form of an expression vector capable of self-replication. Additionally, the polynucleotide may be introduced into a host cell as it is, and operably connected to a sequence essential for its expression in the host cell. Additionally, as used herein, the term "operably connected" refers to a functional connection between a promoter sequence, which initiates and mediates the transcription of the polynucleotide encoding the target protein, and the gene sequence.

Then, the modification of the expression regulation sequence for increasing the expression of the polynucleotide, although not particularly limited thereto, may be performed by inducing a variation in the polynucleotide sequence via deletion, insertion, conservative substitution, non-conservative substitution, or a combination thereof so as to further enhance the activity of the expression regulation sequence; or by replacing the polynucleotide sequence with a polynucleotide sequence with a stronger activity. The expression regulation sequence, although not particularly limited thereto, may include a promoter, an operator sequence, a sequence encoding a ribosome-binding domain, and a sequence for regulating termination of transcription and translation, etc. Additionally, a strong exogenous promoter, instead of the original promoter, may be connected to the upper end of the expression unit of the polynucleotide.

Furthermore, the modification of the polynucleotide sequence on the chromosome, although not particularly limited thereto, may be performed by inducing a variation on the expression regulation sequence of the polynucleotide sequence via deletion, insertion, conservative substitution, non-conservative substitution, or a combination thereof so as to further enhance the activity of the polynucleotide sequence; or by replacing the polynucleotide sequence with an enhanced polynucleotide sequence with a stronger activity.

Generally, the introduction and enhancement of the protein activity may increase the activity or concentration of the corresponding protein relative to the activity or concentration of a wild-type protein or in a microorganism from at least 1%, 10%, 25%, 50%, 75%, 100%, 150%, 200%, 300%, 400%, or 500%, to a maximum of 1000% or 2000%.

Additionally, the microorganism may be one in which the activity of the endogenous homoserine O-succinyltransferase was attenuated or inactivated compared to that of the endogenous activity, in order to enhance the biosynthesis pathway of O-acetyl homoserine by blocking the pathway of biosynthesizing O-succinyl homoserine from homoserine.

The attenuation and inactivation of the homoserine O-succinyltransferase activity may be performed according to the method explained above.

In an exemplary embodiment of the present invention, the O-acetyl homoserine-producing microorganism may be one in which the activity of an enzyme involved in the biosynthesis pathway from phosphoenolpyruvate to homoserine is additionally introduced or enhanced, in order to further increase the amount of homoserine, a substrate for the biosynthesis of O-acetyl homoserine.

Specifically, the above microorganism may be one, in which the activity of at least one protein selected from the group consisting of phosphoenolpyruvate carboxylase (ppc, EC 4.1.1.31), aspartate aminotransferase (aspC, EC 2.6.1.1), and aspartate semialdehyde dehydrogenase (asd, EC 1.2.1.11) is further introduced or enhanced.

For example, ppc gene encoding phosphoenolpyruvate carboxylate including an amino acid sequence represented by SEQ ID NO: 20, aspC gene encoding aspartate aminotransferase including an amino acid sequence represented by SEQ ID NO: 21, and asd gene encoding aspartate semialdehyde dehydrogenase including an amino acid represented by SEQ ID NO: 22 may be introduced into a microorganism. For example, the activities of the three different enzymes may be introduced and enhanced by making all the genes encoding the three different enzymes present in the chromosome of a host cell with a copy number of at least 2, but is not limited thereto. The introduction and enhancement of the activities may be performed according to the method described above.

In an exemplary embodiment of the present invention, the activity of citrate synthase protein was attenuated or inactivated by various methods, which includes deleting the citrate synthase gene in a microorganism of *E. coli* producing O-acetyl homoserine; introducing the gene encoding the modified citrate synthase protein, whose activity was attenuated compared to that of a wild-type, into the position of the citrate synthase gene; and introducing an expression vector for citrate synthase gene antisense RNA. As a result, the thus-constructed O-acetyl homoserine-producing microorganism, in which the activity of citrate synthase protein was attenuated or inactivated, showed an improved O-acetyl homoserine production capability, compared to that of the parent microorganism (Examples 1 to 4).

In another aspect, the present invention provides a method for producing O-acetyl homoserine using an O-acetyl homoserine-producing microorganism with an improved production capability of O-acetyl homoserine. Specifically, the present invention provides a method for producing O-acetyl homoserine including (a) culturing the microorganism; and (b) recovering O-acetyl homoserine produced during the cultivation of the microorganism.

The method of cultivation of the *E. coli* having O-acetyl homoserine production capability according to the present invention may be performed according to the suitable media and culture conditions known in the art. The cultivation process may be easily adjusted by a skilled person in the art depending on the microorganism to be selected. In particular, since the microorganism of the present invention is a microorganism where the activity of the citrate synthase, which is an enzyme mediating the first step of the TCA cycle, is attenuated or inactivated, the cultivation medium may include glutamate, but is not specifically limited thereto.

Examples of the culture methods may include a batch culture, a continuous culture, and a fed-batch culture, but are not limited thereto. These various methods are, for example, disclosed in "Biochemical Engineering" by James M. Lee, Prentice-Hall International Editions, pp 138-176.

The medium used in the cultivation may appropriately meet the requirement of a specific microorganism. Specifically, examples of the microorganism culture media are disclosed in "Manual of Methods for General Bacteriology" by the American Society for Bacteriology, Washington, D.C., 1981. The culture media may be those which include an appropriate carbon source, phosphorous source, inorganic compound, amino acid, and/or vitamins, etc, and cultivation may be performed in aerobic conditions while adjusting temperature, pH, etc.

Examples of the carbon source may include carbohydrates such as glucose, lactose, sucrose, lactic acid, fructose, maltose, starch, and cellulose; fats such as soybean oil, sunflower oil, castor oil, berber oil, and coconut oil; fatty acids such as palmitic acid, stearic acid, and linoleic acid; alcohols such as glycerol and ethanol; and organic acids such as acetic acid. These carbon sources may be used alone or in combination, but are not limited thereto.

Examples of the nitrogen source may include organic nitrogen sources such as peptone, yeast extract, gravy, malt extract, corn steep liquor (CSL), and bean flour; and inorganic nitrogen sources such as urea, ammonium sulfate, ammonium chloride, ammonium phosphate, ammonium carbonate, and ammonium nitrate. These nitrogen sources may be used alone or in combination, but are not limited thereto. The culture media may further include, as a phosphorous source, potassium dihydrogen phosphate, dipotassium hydrogen phosphate, and corresponding sodium-containing salts. The culture media may include metals such as magnesium sulfate and iron sulfate. Additionally, amino acids, vitamins and appropriate precursors may be included. These culture media or precursors may be added to the culture in the form of a batch culture or continuous culture, but are not limited thereto.

Additionally, the pH of the culture may be adjusted by adding a compound such as ammonium hydroxide, potassium hydroxide, ammonia, phosphoric acid, and sulfuric acid during cultivation in an appropriate manner. Additionally, bubble formation may be prevented during the cultivation using an antifoaming agent such as fatty acid polyglycol ester. Additionally, in order to maintain aerobic conditions in a culture liquid, an oxygen gas or a gas (e.g., air) containing an oxygen gas may be added to a culture. The culture temperature may be from 20° C. to 45° C., and specifically from 25° C. to 40° C., but is not limited thereto. The cultivation may be continued until the production of O-acetyl homoserine reaches the intended level, and specifically for 10 hours to 160 hours, but is not limited thereto.

The method of producing O-acetyl homoserine of the present invention may further include recovering O-acetyl homoserine from the cultured microorganism or a cultured product thereof. The recovery of the intended O-acetyl homoserine may be performed by a microorganism cultivation method according to the present invention, for example, an appropriate method known in the art such as a batch culture, a continuous culture, and a fed-batch culture.

The recovery may include a purification step.

The thus-recovered O-acetyl homoserine can produce methionine by a two-step process (Korean Patent No. 10-0905381).

The two-step process includes a process of producing L-methionine and an organic acid by an enzyme reaction using an enzyme having the O-acetyl homoserine sulfhydrylase activity or a microorganism possessing the enzyme, while using the O-acetyl homoserine, which was produced by the L-methionine precursor-producing microorganism, and methyl mercaptan as substrates.

More specifically, the present invention provides a method for producing L-methionine by an enzyme reaction of O-acetyl homoserine sulfhydrylase, etc., using O-acetyl homoserine, which was accumulated by the above method, as a substrate.

In the second step, when O-acetyl homoserine is used as an L-methionine precursor, O-acetyl homoserine sulfhydrylase derived from a microorganism, specifically belonging to *Leptospira* sp., *Chromobacterium* sp., and *Hyphomonas* sp., and more specifically belonging to *Leptospira meyeri*, *Pseudomonas aurogenosa*, *Hyphomonas Neptunium*, and *Chromobacterium Violaceum* may be used.

The reaction is the same as shown below.

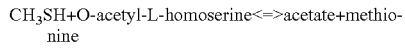

The additional process for producing methionine is disclosed in Korean Patent No. 10-0905381, and the entire specification of the patent may be included as a reference in the present invention.

MODE FOR INVENTION

Hereinafter, the present invention will be described in more detail with reference to the following Examples. However, these Examples are for illustrative purposes only, and the invention is not intended to be limited by these Examples.

REFERENCE EXAMPLE

Construction of O-Acetyl Homoserine-Producing Microorganism

<1-1> Deletion of metB Gene Derived from Wild-Type *E. coli* (International Publication No. WO 2008/013432)

An O-acetyl homoserine-producing microorganism was constructed using *E. coli*, a representative microorganism among *Escherichia* sp. To this end, wild-type *E. coli* K12 W3110 (ATCC27325) obtained from American Type Culture Collection (ATCC) was used. First, in order to block the synthesis pathway from O-succinyl-L-homoserine to cystathionine, cystathionine synthase-encoding metB gene (SEQ ID NO: 10) was deleted. Specifically, the cystathionine synthase-encoding metB gene was deleted via an FRT-one-step PCR deletion method (PNAS (2000) vol 97: P6640-6645).

Specifically, the metB deletion cassette was constructed via a PCR reaction based on the pKD3 vector (PNAS (2000) vol 97: P6640-6645) as a template using primers of SEQ ID NOS: 30 and 31 as follows: 30 cycles of denaturation at 94° C. for 30 seconds, annealing at 55° C. for 30 seconds, and extension at 72° C. for 1 minute. The resulting PCR product was electrophoresed on a 1.0% agarose gel, and a 1.2 kb DNA band obtained therefrom was purified. The recovered DNA fragment was electroporated into *E. coli* (K12) W3110, which was already transformed with the pKD46 vector (PNAS (2000) vol 97: P6640-6645). For electroporation, the W3110 strain transformed with the pKD46 was cultured in an LB medium containing 100 μg/L ampicillin and 5 mM arabinose (L-arabinose) at 30° C. until $OD_{600}$=0.6, and used after washing twice with sterile distilled water and once with 10% glycerol. Electroporation was performed at 2500 V. The recovered strain was streaked on an LB plate containing 25 μg/L chloramphenicol, cultured at 37° C. overnight, and the strain showing resistance was selected. The selected strain was subjected to a PCR reaction under the same conditions based on the strain as a template using the same primers, and the deletion of metB gene was confirmed by observing the gene size of 1.2 kb on a 1.0% agarose gel. The thus-confirmed strain was cultured in an LB medium after transforming again with the pCP20 vector (PNAS (2000) vol 97: P6640-6645), and the final metB gene-deleted strain, where the gene size was reduced to 150 bp on a 1.0% agarose gel through PCR performed under the same conditions, was constructed and the removal of the chloramphenicol marker was confirmed. The thus-constructed strain was designated as "W3-B".

<1-2> Deletion of thrB Gene (International Publication No. WO 2008/013432)

In an effort to increase the amount of O-succinylhomoserine synthesis from homoserine, thrB gene, which is a homoserine kinase-encoding gene, was deleted. For deletion of the thrB gene from the W3-B strain constructed in Example 1, the FRT one step PCR deletion method used in the deletion of metB gene was used.

A thrB deletion cassette was constructed via PCR based on the pKD4 vector (PNAS (2000) vol 97: P6640-6645) as a template using primers of SEQ ID NOS: 32 and 33 as follows: 30 cycles of denaturation at 94° C. for 30 seconds, annealing at 55° C. for 30 seconds, and extension at 72° C. for 1 minute.

The resulting PCR product was electrophoresed on a 1.0% agarose gel, and a 1.6 kb DNA band obtained therefrom was purified. The recovered DNA fragment was electroporated into W3-B strain, which was already transformed with the pKD46 vector. The recovered strain was streaked on an LB plate containing 50 μg/L kanamycin, cultured at 37° C. overnight, and the strain showing resistance was selected.

The selected strain was subjected to a PCR reaction under the same conditions directly based on the strain as a template using the same primers of SEQ ID NOS: 32 and 33, and confirmed the deletion of thrB gene by selecting the strain having the gene size of 1.6 kb on a 1.0% agarose gel. The thus-confirmed strain was cultured in an LB medium after transforming again with the pCP20 vector, and the final thrB gene-deleted strain, where the gene size was reduced to 150 bp on a 1.0% agarose gel through PCR performed under the same conditions, was constructed and the removal of the kanamycin marker was confirmed. The thus-constructed strain was designated as "W3-BT".

<1-3> A Variant metA with Homoserine Acetyltransferase Activity (International Publication No. WO 2012/087039)

In order to strengthen the homoserine acetyltransferase activity in the strain obtained in Reference Example <1-2>, it was intended to introduce mutant type metA gene (SEQ ID NOS: 24 and 26) encoding homoserine acetyltransferase.

First, in order to construct the variant of metA gene with a strengthened activity, a PCR reaction was performed based on the chromosome of a wild-type strain W3110 as a template using the primers of SEQ ID NOS: 34 and 35, and the metA gene encoding homoserine O-succinyltransferase was amplified.

The primers used in the PCR reaction were prepared based on the polynucleotide sequence of the E. coli chromosome, NC_000913, registered in the NIH Gene Bank, and the primers of SEQ ID NOS: 34 and 35 have the EcoRV and HindIII restriction sites, respectively. The thus-obtained PCR product and the pCL1920 plasmid including Pcj1 were respectively treated with EcoRV and HindIII, and the PCR product was cloned into the pCL1920 plasmid. E. coli DH5α was transformed using the cloned plasmid, and the transformed E. coli DH5α was selected on LB plates containing 50 μg/mL spectinomycin, and the plasmid was obtained therefrom. The thus-obtained plasmid was designated as "pCL_Pcj1_metA".

Then, the 111$^{th}$ amino acid, glycine (Gly), of O-succinyltransferase was substituted with glutamic acid (Glu) (G111E) based on the above-constructed pCL_Pcj1_metA plasmid as a template using a site directed mutagenesis kit (Stratagene, USA). The thus-constructed plasmid including the variant of G111E metA gene was designated as "pCL_Pcj1_metA (EL)".

Additionally, in order to substitute the 111$^{th}$ amino acid of O-succinyltransferase from glycine to glutamic acid, and the 112$^{nd}$ amino acid from leucine to histidine, primers of SEQ ID NOS: 38 and 39 were used. The plasmid including metA gene, in which the 111$^{th}$ amino acid was substituted from glycine to glutamic acid, and the 112$^{nd}$ amino acid was substituted from leucine to histidine was designated as "pCL_Pcj1_metA (EH)".

Then, a replacement cassette, for the replacement with metA (EH) into a strain, was constructed via PCR using pKD3 vector as a template along with primers of SEQ ID NOS: 40 and 41 as follows: 30 cycles of denaturation at 94° C. for 30 seconds, annealing at 55° C. for 30 seconds, and extension at 72° C. for 2 minutes. The respective PCR product was obtained using pCL-Pcj1-metA (EH) as a template for the metA (EH) part of the replacement cassette along with primers of SEQ ID NOS: 42 and 43, and primers of SEQ ID NOS: 42 and 45 for the wild-type metA part. metA (EH) replacement cassettes including the chloramphenicol marker part were constructed using the three different PCR products along with the primers of SEQ ID NOS: 42 and 45, and electroporated into W3-BT strain, which was already transformed with the pKD46 vector, constructed in Reference Example <1-2>. The thus-confirmed strain was cultured in an LB medium after transforming again with the pCP20 vector, and the strain, where the chloramphenicol marker was removed, and metA gene was substituted with metA (EH) was designated as "W3-BTA".

<1-4> Construction of a Strain with 2 Copies of ppc, aspC, and asd Genes (European Patent Application Publication No. EP 2290051)

In order to increase the O-acetyl homoserine-producing capability of W3-BTA strain constructed in Reference Example <1-3>, the biosynthetic pathway was enhanced by citing the prior filed patent EP 2290051. In the same manner as in the above EP patent, a strain having 2 amplified copies each of the genes, i.e., the ppc gene encoding phosphoenolpyruvate carboxylase using primers of SEQ ID NOS: 46, 47, 48, and 49; the aspC gene encoding aspartate aminotransferase using primers of SEQ ID NOS: 50 and 51; and the asd gene encoding aspartate semialdehyde dehydrogenase using primers of SEQ ID NOS: 52, 53, 54, and 55, was constructed. In particular, the above strain with an enhanced biosynthetic pathway while producing O-acetyl homoserine was designated as "W3-BTA2PCD" (also called "WCJM").

<1-5> Flask-Culture Experiments

The amount of O-acetyl homoserine production by the strain constructed in Reference Examples <1-3> and <1-4> was tested by an Erlenmeyer flask-culture.

Specifically, W3110, W3-BTA, and WCJM strains were inoculated into LB media, and cultured at 33° C. overnight. Then, a single colony thereof was inoculated into 3 mL of LB medium, cultured at 33° C. for 5 hours, diluted 200-fold in a 250 mL Erlenmeyer flask containing 25 mL of an O-acetyl homoserine-producing medium, cultured at 33° C. at a rate of 200 rpm for 30 hours, and the amount of O-acetyl homoserine production was examined via HPLC analysis. The media compositions used are shown in Table 1 below, and the amount of O-acetyl homoserine production examined is shown in Table 2 below.

TABLE 1

Composition of O-acetyl homoserine-producing flask-culture

| Composition | Conc. (per liter) |
|---|---|
| glucose | 40 g |
| (NH$_4$)$_2$SO$_4$ | 17 g |
| KH$_2$PO$_4$ | 1.0 g |
| MgSO$_4$•7H$_2$O | 0.5 g |
| FeSO$_4$•7H$_2$O | 5 mg |
| MnSO$_4$•8H$_2$O | 5 mg |
| ZnSO$_4$ | 5 mg |
| CaCO$_3$ | 30 g |
| yeast extract | 2 g |
| methionine | 0.15 g |
| threonine | 0.15 g |

TABLE 2

| | OD (562 nm) | Glucose consumption (g/L) | O-Acetyl homoserine (g/L) |
|---|---|---|---|
| W3110 | 14.2 | 40 | 0 |
| W3-BTA | 8.4 | 36 | 0.9 |
| WCJM | 9.6 | 35 | 1.2 |

The result revealed that the wild-type W3110 did not produce O-acetyl homoserine at all, whereas the W3-BTA strain produced 0.9 g/L of O-acetyl homoserine and the WCJM strain, which was strengthened with the biosynthesis pathway, produced 1.2 g/L of O-acetyl homoserine.

Example 1

Deletion of Citrate Synthase Activity

<1-1> Construction of a Citrate Synthase Gene-Deleted Microorganism in an O-Acetyl Homoserine-Producing Microorganism Citrate synthase (GltA) is the enzyme in the first step of the TCA cycle, and starts with the reaction between oxaloacetate and acetyl-CoA. The growth inhibition by decrease in the TCA cycle is well known (Meded Rijksuniv Gent Fak Landbouwkd Toegep Biol Wet. 2001; 66(3a): 333-6). However, in order to increase the amount of acetyl-CoA used as a substrate for O-acetyl homoserine, W3-BTA and WCJM strains where citrate synthase activity is deleted were to be produced.

Specifically, the citrate synthase gene in W3-BTA and WCJM strains was deleted via PCR based on pKD4 vector as a template using primers of SEQ ID NOS: 56 and 57 as follows: 30 cycles of denaturation at 94° C. for 30 seconds, annealing at 55° C. for 30 seconds, and extension at 72° C. for 2 minutes. The resulting PCR product was electrophoresed on a 1.0% agarose gel, and the size of the gene was confirmed to be 1.6 kb, and its DNA was purified. The recovered DNA fragments were electroporated into W3-BTA and WCJM strains, which were already transformed with the pKD46 vector. For electroporation, W3-BTA and WCJM strains, transformed with the pKD46 vector, were cultured in an LB medium containing 100 µg/L ampicillin and 5 mM arabinose at 30° C. until $OD_{600}$=0.6, and washed twice with distilled water and once with 10% glycerol to be used. Electroporation was performed at 2500 V. The thus-recovered strains were streaked on LB plates containing 50 µg/L kanamycin, cultured at 37° C., and the strains showing resistance were selected.

The selected strains were subjected to PCR using the primers of SEQ ID NOS: 58 and 59 under the same conditions, electrophoresed on a 1.0% agarose gel, and the size of the gene was observed to be 2.5 kb, thereby confirming that a deletion cassette was inserted into the citrate synthase gene portion on the chromosome. The thus-confirmed strains were transformed again with the pCP20 vector, cultured in LB media, and strains having a deletion of the citrate synthase gene, whose size was reduced to 1.1 kb on a 1.0% agarose gel, were constructed by PCR, and it was confirmed that kanamycin markers were removed. The thus-constructed strains were designated as "W3-BTA-AD" and "WCJM-AD", respectively.

<1-2> Evaluation of a Citrate Synthase Gene-Deleted Microorganism in an O-Acetyl Homoserine-Producing Microorganism W3-BTA-AD and WCJM-AD strains can grow in an LB medium, but due to the deletion of the citrate synthase gene, they could not grow in an O-acetyl homoserine-containing medium. In order to test the amount of O-acetyl homoserine production, an Erlenmeyer flask-culture was performed under the condition (Table 3—a composition adding glutamate in the medium) of adding 3 g/L of glutamate into the existing composition of the culture medium.

Specifically, W3-BTA-AD and WCJM-AD strains were inoculated into LB media and cultured at 33° C. overnight. Then, a single colony thereof was inoculated into 3 mL of LB medium, cultured at 33° C. for 5 hours, diluted 200-fold in a 250 mL Erlenmeyer flask containing 25 mL of an O-acetyl homoserine-producing medium (with glutamate added), cultured at 33° C. at a rate of 200 rpm for 30 hours, and the amount of O-acetyl homoserine production was examined via HPLC analysis. The amount of O-acetyl homoserine production examined is shown in Table 4 below.

TABLE 3

Composition of a medium with glutamate added to a basal medium

| Composition | Conc. (per liter) |
|---|---|
| glucose | 40 g |
| $(NH_4)_2SO_4$ | 17 g |
| $KH_2PO_4$ | 1.0 g |
| $MgSO_4 \cdot 7H_2O$ | 0.5 g |
| $FeSO_4 \cdot 7H_2O$ | 5 mg |
| $MnSO_4 \cdot 8H_2O$ | 5 mg |
| $ZnSO_4$ | 5 mg |
| $CaCO_3$ | 30 g |
| yeast extract | 2 g |
| methionine | 0.15 g |
| threonine | 0.15 g |
| glutamate | 3 g |

TABLE 4

Production of O-acetyl homoserine via flask-culture

| | OD (562 nm) | Glucose consumption (g/L) | O-acetyl homoserine (g/L) | Glutamate (g/L) |
|---|---|---|---|---|
| W3-BTA | 9.9 | 38 | 0.9 | 3.2 |
| W3-BTA-AD | 6.1 | 34 | 1.4 | 2.3 |
| WCJM | 9.2 | 37 | 1.3 | 3.5 |
| WCJM-AD | 5.6 | 33 | 2.1 | 1.7 |

The result of the O-acetyl homoserine production via flask-culture revealed that the W3-BTA strain produced 0.9 g/L of O-acetyl homoserine, and W3-BTA-AD produced 1.4 g/L of O-acetyl homoserine, which is a 55.6% increase, although it showed a decrease in its glucose consumption. The WCJM strain produced 1.3 g/L of O-acetyl homoserine while the WCJM-AD strain produced 2.1 g/L of O-acetyl homoserine, thus confirming that the O-acetyl homoserine production capability was improved by 61.5% due to the deletion of the citrate synthase gene.

Example 2

Attenuation of the Activity of Citrate Synthase Protein

<2-1> Kinds of Citrate Synthase Gene Modifications

The WCJM-AD strain constructed in Example <1-1> showed a low culture rate, and three different types of variants, which showed an attenuated activity and a reduced binding ability to acetyl-CoA according to various modifications of citrate synthase known in numerous references (The Journal of Biological Chemistry, 2003, 278, 35435-35443), were selected. The information on the three different types of variants is shown in Table 5, which shows modified genes in which the $145^{th}$ amino acid, tyrosine (Y), was substituted with alanine (A), and the $167^{th}$ amino acid, lysine (K), was substituted with alanine (A), and the $204^{th}$ amino acid, threonine (T), was substituted with alanine (A).

TABLE 5

Evaluation on citrate synthase (gltA) variants

| | KM VALUE [mM] | |
|---|---|---|
| | Acetyl-CoA | OAA |
| WT | 0.12 | 0.026 |
| Y145A | 0.23 | 0.051 |
| K167A | 0.22 | 0.037 |
| T204A | 0.21 | 0.004 |

<2-2> Construction of a Microorganism with Attenuated Citrate Synthase Protein Activity in an O-Acetyl Homoserine-Producing Microorganism The present inventors intended to increase the production capability by introducing the variants, in which the activity of citrate synthase protein was attenuated as explained in Example <2-1>, into the O-acetyl homoserine-producing microorganism.

In order to introduce the three different types of citrate synthase gene variants into the WCJM-AD strain, a modification replacement cassette was designed as shown in FIG. 1. Each variant was synthesized by substituting a primer with a nucleotide, and each cassette was constructed through 3 PCR products. For the citrate synthase gene portion, the W3110 strain was used as a template, and the modification on the 145$^{th}$ amino acid produced PCR reactions were performed using the primers of SEQ ID NOS: 60 and 63 and SEQ ID NOS: 62 and 61, respectively, and obtained PCR products with a size of 514 bp and 1,112 bp.

Likewise, the modification on the 167$^{th}$ amino acid produced PCR products with a size of 580 bp and 1,046 bp using the primers of SEQ ID NOS: 60 and 65, and the primers of SEQ ID NOS: 64 and 61, and the modification on the 204$^{th}$ amino acid produced PCR products with a size of 688 bp and 936 bp using the primers of SEQ ID NOS: 60 and 67 and SEQ ID NOS: 66 and 61. For the common kanamycin portion, PCR reactions were performed based on the pKD4 vector as a template using the primers of SEQ ID NOS: 68 and 69. In particular, for the insertion into the position of the citrate synthase gene, the cassette was constructed so as to include the polynucleotide sequence downstream of the citrate synthase gene in the SEQ ID NO: 69, and a PCR product with a size of 1,571 bp was obtained via electrophoresis. A sewing PCR reaction was performed based on the kanamycin DNA fragment, which is the common part with each of the two DNA fragments collected according to the modifications, respectively, using the primers of SEQ ID NOS: 60 and 69, as follows: 30 cycles of denaturation at 94° C. for 30 seconds, annealing at 55° C. for 30 seconds, and extension at 72° C. for 4 minutes. Each of the final PCR products was confirmed on a 1.0% agarose gel, and the DNA fragments with a size of 3,115 bp for the three different kinds of cassettes of citrate synthase gene modifications. The collected DNA fragments were electroporated into the WCJM-AD strain, which was already transformed with the pKD46 vector. For electroporation, the W3110 strain transformed with the pKD46 was cultured in an LB medium containing 100 µg/L ampicillin and 5 mM arabinose at 30° C. until OD$_{600}$=0.6, and used after washing twice with sterile distilled water and once with 10% glycerol. Electroporation was performed at 2500 V. The recovered strain was streaked on an LB plate containing 25 µg/L kanamycin, cultured at 37° C. overnight, and the strain showing resistance was selected. The selected strain was subjected to a PCR reaction under the same conditions based on the strain as a template using the same primers of SEQ ID NOS: 58 and 59, and confirmed the deletion of metB gene by observing the gene size of 3.7 kb on a 1.0% agarose gel, thereby confirming that a modification cassette, in which the amino acid of the citrate synthase gene was substituted, was inserted. The thus-confirmed strain was cultured in an LB medium after transforming again with the pCP20 vector, and the three variant strains regarding the citrate synthase activity, where the gene size was reduced to 2.5 kb on a 1.0% agarose gel through PCR performed under the same conditions, were constructed and the removal of the kanamycin marker was confirmed. The thus-constructed strains were designated as "WCJM-A145", "WCJM-A167", and "WCJM-A204", and the sequence information of the citrate synthase gene introduced with modifications are shown in SEQ ID NOS: 1 to 3 (amino acid sequences) and SEQ ID NOS: 5 to 7 (nucleotide sequences), respectively.

<2-3> Evaluation of Microorganisms with Attenuated Citrate Synthase Activity in O-Acetyl Homoserine-Producing Microorganisms An Erlenmeyer flask-culture was performed in order to examine the amount of O-acetyl homoserine production by three different strains of WCJM-A145, WCJM-A167, and WCJM-A204, in which the activity of the citrate synthase gene was attenuated. Four kinds of strains, i.e., WCJM-A145, WCJM-A167, and WCJM-A204 strains including the WCJM strain, were inoculated into LB media, and cultured at 33° C. overnight. Then, a single colony thereof was inoculated into 3 mL of LB medium, cultured at 33° C. for 5 hours, diluted 200-fold in a 250 mL Erlenmeyer flask containing 25 mL of an O-acetyl homoserine-producing medium, cultured at 33° C. at a rate of 200 rpm for 30 hours, and the amount of O-acetyl homoserine production was examined via HPLC analysis. The results are shown in Table 6 below.

TABLE 6

Production of O-acetyl homoserine via flask-culture

| | OD (562 nm) | Glucose consumption (g/L) | O-acetyl homoserine (g/L) | Glutamate (g/L) |
|---|---|---|---|---|
| WCJM | 8.9 | 35 | 1.3 | 1.3 |
| WCJM-A145 | 7.4 | 35 | 2.0 | 0 |
| WCJM-A167 | 6.3 | 29 | 1.9 | 0 |
| WCJM-A204 | 9.1 | 40 | 1.1 | 1.8 |

The result of O-acetyl homoserine production via flask-culture revealed that the WCJM strain produced 1.3 g/L of O-acetyl homoserine, and the two strains, WCJM-A145 and WCJM-A167, produced 2.0 g/L and 1.9 g/L of O-acetyl homoserine, respectively, while the amount of their glucose consumption decreased along with the decrease in their absorbance (OD). Considering the specific decrease of glutamate from 1.3 g/L to 0 g/L, it was confirmed that the result is due to the decrease in TCA cycle flow caused by the attenuation in the citrate synthase activity. However, the WCJM-A204 strain showed an increase in glutamate while showing a decrease in the amount of O-acetyl homoserine production to 0.2 g/L, thus confirming the modification is one with a strengthened activity.

Example 3

Attenuation in Expression of Citrate Synthase Protein

<3-1> Construction of Expression Vector for Citrate Synthase Gene Antisense RNA (asRNA)

The present inventors made an effort to apply an antisense RNA (asRNA) technology in order to attenuate the expression of citrate synthase protein. The antisense RNA technology is a method for reducing protein expression by neutralizing the binding between citrate synthase mRNA and ribosome, via overexpression of the complementary binding portion to the citrate synthase mRNA of the target gene. This method has the advantage in that it can regulate the level of inhibition by controlling the binding force with the mRNA of the citrate synthase gene, and this method is also useful for the construction of a recombinant microorganism because this method can effectively construct and reduce gene expression via antisense RNA controlling gene expression, not necessitating the conventional process of gene deletion.

The vector construction was performed referring to a reference (Methods Mol Biol. 2012; 815:307-19. doi: 10.1007/978-1-61779-424-7_23.), and for overexpression, the antisense RNA region of the synthase gene was to be introduced into the pBAD24 plasmid capable of induction. The pBAD24-citrate synthase asRNA vector map is shown in FIG. 2. The region where the antisense RNA of the citrate synthase gene was expressed has a size of 100 bp including the 52 bp region of the promoter region and the 48 bp region from the initiation codon of the citrate synthase, and a 38 bp paired termini (PT) structure, which reduces the instability of the antisense RNA (asRNA), is connected to both flanking regions. The antisense RNA region of the citrate synthase gene was obtained using the primers of SEQ ID NOS: 70 and 71, and the NcoI and HindIII restriction sites were included to be cloned into a vector.

The thus-obtained PCR product had a size of 194 bp, and the PCR product was cloned into the pBAD24 plasmid after treating them with EcoRV and HindIII, respectively. The thus-cloned plasmid was used to transform *E. coli* DH5α, and the transformed *E. coli* DH5α was selected from the LB plates containing 100 µg/mL of ampicillin, and obtained the plasmid therefrom. The thus-obtained plasmid was designated as "pBAD24-gltA asRNA".

<3-2> Introduction of an Expression Vector of Antisense RNA of Citrate Synthase Gene into an O-Acetyl Homoserine-Producing Microorganism and Evaluation Thereof The pBAD24-gltA-asRNA, an expression vector of antisense RNA of citrate synthase gene, was transformed into the WCJM strain, which is an O-acetyl homoserine-producing microorganism. Here, the transformed strain was designated as "WCJM/A-asRNA". In particular, it was attempted to control the expression amount of the citrate synthase protein by controlling the expression amount of the antisense RNA of the citrate synthase, and here, the expression amount of the antisense RNA can be controlled according to the concentration of arabinose.

As a result, it was confirmed that the amount of the O-acetyl homoserine production increased when the activity of the citrate synthase was attenuated as in Example 2.

Additionally, an Erlenmeyer flask-culture was performed to examine whether the amount of O-acetyl homoserine production increases as the expression amount of the citrate synthase decreases.

Specifically, WCJM and WCJM/A-asRNA strains were inoculated into LB media, and cultured at 33° C. overnight. Then, a single colony thereof was inoculated into 3 mL of LB medium, cultured at 33° C. for 5 hours, diluted 200-fold in a 250 mL Erlenmeyer flask containing 25 mL of an O-acetyl homoserine-producing medium. In particular, in order to control the expression amount of antisense RNA of the citrate synthase, arabinose was added at concentrations of 0 mM, 2 mM, and 5 mM, and cultured at 33° C. at a rate of 200 rpm for 15 hours and 30 hours. The amount of O-acetyl homoserine production was examined via HPLC analysis, and the results are shown in Tables 7 and 8 below.

TABLE 7

| 15 Hours | Arabinose | OD (562 nm) | Glucose consumption (g/L) | O-acetyl homoserine (g/L) |
|---|---|---|---|---|
| WCJM | 0 mM | 4.2 | 9.7 | 0.5 |
| WCJM | 2 mM | 4.5 | 8.9 | 0.6 |
| WCJM | 5 mM | 4.7 | 8.9 | 0.5 |
| WCJM/A-asRNA | 0 mM | 4.5 | 10.1 | 0.6 |
| WCJM/A-asRNA | 2 mM | 4.2 | 8.8 | 0.6 |
| WCJM/A-asRNA | 5 mM | 3.4 | 6.9 | 0.5 |

TABLE 8

| 30 Hours | Arabinose | OD (562 nm) | Glucose consumption (g/L) | O-acetyl homoserine (g/L) |
|---|---|---|---|---|
| WCJM | 0 mM | 8.9 | 32 | 1.4 |
| WCJM | 2 mM | 9.1 | 34 | 1.3 |
| WCJM | 5 mM | 8.9 | 33 | 1.3 |
| WCJM/A-asRNA | 0 mM | 9.2 | 33 | 1.3 |
| WCJM/A-asRNA | 2 mM | 8.8 | 32 | 1.6 |
| WCJM/A-asRNA | 5 mM | 7.1 | 29 | 1.7 |

As a result, it was confirmed that, when cultured for 15 hours, the WCJM/A-asRNA strain showed a decrease in OD by about 1 according to the concentration of arabinose, whereas the concentration of O-acetyl homoserine was similar. However, when cultured for 30 hours, the WCJM strain, which is a control strain, showed the same OD and O-acetyl homoserine concentration even when the concentration of arabinose increased, whereas the WCJM/A-asRNA strain, which is a strain introduced with the expression vector for citrate synthase RNA antisense, showed a marked difference as the concentration of arabinose increased. The OD was 9.2 when the arabinose concentration was 0 mM, whereas the OD was 7.1 at 5 mM of the arabinose concentration, a decrease of 5.1, and the amount of O-acetyl homoserine increased by 30.8% although the glucose consumption was small. From these results, it was confirmed that not only the attenuation in citrate synthase activity but also in the attenuation in protein expression exhibit the same results.

Example 4

Attenuation and Inactivation of Citrate Synthase Activity in a Microorganism with High Production Yield of O-Acetyl Homoserine <4-1> Construction of a Microorganism with High O-Acetyl Homoserine Production Yield with Inactivated Citrate Synthase Activity and Evaluation Thereof International Publication No. WO 2012/087039 discloses in detail a method for constructing an O-acetyl homoserine-producing microorganism from a threonine-producing microorganism derived from a wild-type W3110 strain, due to NTG mutation. In particular, the constructed strain producing O-acetyl homoserine with high yield was deposited at Korean Culture Center of Microorganisms (KCCM) under the Accession No of KCCM 11146P.

The KCCM11146P strain can consume 40 g/L of glucose during a flask-culture and produces about 15 g/L to 16 g/L of O-acetyl homoserine and is thus regarded as having high O-acetyl homoserine production capability. Accordingly, in order to examine whether the strain produces a higher yield of O-acetyl homoserine when the citrate synthase activity is deleted, the same was applied to the KCCM11146P strain. The construction method was the same as in Example <1-1>, and by this method, the KCCM11146P strain, where the citrate synthase activity was deleted, was constructed and designated as "KCCM11146P-AD".

The amount of O-acetyl homoserine production by the KCCM11146P strain, where the citrate synthase activity was deleted, was tested by an Erlenmeyer flask-culture. The KCCM11146P or KCCM11146P-AD strain was inoculated into an LB medium and cultured at 33° C. overnight. Then, a single colony thereof was inoculated into 3 mL of LB medium, cultured at 33° C. for 5 hours, diluted 200-fold in a 250 mL Erlenmeyer flask containing 25 mL of an O-acetyl homoserine-producing medium (with glutamate added), and cultured at 33° C. at a rate of 200 rpm for 30 hours. The amount of O-acetyl homoserine production was examined via HPLC analysis, and the results are shown in Table 9 below.

TABLE 9

Production of O-acetyl homoserine via flask-culture

| | OD (562 nm) | Glucose consumption (g/L) | O-acetyl homoserine (g/L) | Glutamate (g/L) |
|---|---|---|---|---|
| KCCM11146P | 18.3 | 60 | 14.2 | 4.6 |
| KCCM11146P-AD | 14.6 | 60 | 16.7 | 1.8 |

The result of O-acetyl homoserine production via flask-culture revealed that the KCCM11146P strain produced 14.2 g/L of O-acetyl homoserine, and the KCCM11146P-AD strain produced 16.7 g/L of O-acetyl homoserine, a 17.6% increase, although it showed a decrease in absorbance (OD).

<4-2> Construction of a Microorganism with High O-Acetyl Homoserine Production Yield with Attenuated Citrate Synthase Activity and Evaluation Thereof In order to examine whether the KCCM11146P strain, which is a strain with high production yield of O-acetyl homoserine, produces a higher yield of O-acetyl homoserine even when the citrate synthase activity is attenuated, the modification on the 145$^{th}$ amino acid (from tyrosine (Y) to alanine (A)) and the modification on the 167$^{th}$ amino acid (from lysine (K) to alanine (A)), which showed the highest O-acetyl homoserine-producing capabilities among the three variant types attenuating the protein activities explained in Example <2-1>, were applied to the KCCM11146P strain.

The construction method was the same as in Example <2-2>, and by the method, two KCCM11146P strains, where the citrate synthase activity was attenuated, were constructed and designated as "KCCM11146P-A145" and "KCCM11146P-A167", respectively.

The amount of O-acetyl homoserine production by the two strains of KCCM11146P-A145 and KCCM11146P-A167, where the citrate synthase activity was attenuated, was tested by an Erlenmeyer flask-culture. The three strains, i.e., KCCM11146P-A145 and KCCM11146P-A167 strains and the KCCM11146P strain, were inoculated into LB media, and cultured at 33° C. overnight. Then, a single colony thereof was inoculated into 3 mL of LB medium, cultured at 33° C. for 5 hours, diluted 200-fold in a 250 mL Erlenmeyer flask containing 25 mL of an O-acetyl homoserine-producing medium, and cultured at 33° C. at a rate of 200 rpm for 30 hours. The amount of O-acetyl homoserine production was examined via HPLC analysis, and the results are shown in Table 10 below.

TABLE 10

Production of O-acetyl homoserine via flask-culture

| | OD (562 nm) | Glucose consumption (g/L) | O-acetyl homoserine (g/L) | Glutamate (g/L) |
|---|---|---|---|---|
| KCCM11146P | 16.3 | 60 | 15.0 | 1.6 |
| KCCM11146P-A145 | 14.6 | 60 | 17.5 | 0 |
| KCCM11146P-A167 | 14.2 | 60 | 17.3 | 0 |

The result of O-acetyl homoserine production via flask-culture revealed that the KCCM11146P strain produced 15.0 g/L of O-acetyl homoserine, and the two strains of KCCM11146P-A145 and KCCM11146P-A167 showed similar results as in Example <2-3>. The two strains respectively produced 17.5 g/L and 17.3 g/L of O-acetyl homoserine, an increase of about 16.7%, although they both showed a decrease in absorbance (OD).

The strain with high production yield of O-acetyl homoserine also showed a decrease in glutamate from 1.6 g/L to 0 g/L, according to the decrease in TCA cycle flow caused by the attenuation in the citrate synthase activity.

These results demonstrate that citrate synthase activity enables production of O-acetyl homoserine by applying the attenuated modification. Additionally, they also indicate that when a conversion reaction is conducted based on the O-acetyl homoserine, which was produced according to the International Publication No. WO2008/013432, as a template, and using a conversion enzyme, which additionally has the activities of cystathionine gamma synthase, O-succinylhomoserine sulfhydrylase, and O-acetyl homoserine sulfhydrylase, it is possible to simultaneously synthesize L-methionine and acetate.

The present inventors confirmed that the KCCM11146P strain, the variant on the 167$^{th}$ amino acid of the citrate synthase, has an improved production of O-acetyl homoserine, designated the KCCM11146P-A167 strain as "CA05-4007", and deposited it at the Korean Culture Center of Microorganisms (KCCM), an international depositary authority under the Budapest Treaty, on Nov. 22, 2013 (Accession No: KCCM 11483P).

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents and other embodiments that may be included within the spirit and scope of the present invention as defined by the appended claims.

The invention claimed is:

1. A microorganism of *Escherichia* sp. producing O-acetyl homoserine, wherein the endogenous activity of citrate synthase is attenuated or inactivated, and a homoserine O-acetyltransferase is further introduced or enhanced, or an endogenous homoserine O-succinyltransferase is further modified to a polypeptide having 95% identity or above with SEQ ID NO: 16 and further having mutations at the G111E position and L112T or L112H positions to have the activity of homoserine O-acetyltransferase, wherein the microorganism has an improved O-acetyl homoserine production capability compared to a corresponding unmodified *Escherichia* sp. microorganism.

2. The microorganism of *Escherichia* sp. according to claim 1, wherein the microorganism with the attenuated endogenous activity of citrate synthase has an amino acid sequence of SEQ ID NO: 1 or SEQ ID NO: 2.

3. The microorganism of *Escherichia* sp. according to claim 1, wherein the activity of cystathionine gamma synthase, homoserine kinase, or both is further attenuated or inactivated compared to their endogenous activities.

4. The microorganism of *Escherichia* sp. according to claim 1, wherein the activity of at least one protein selected from the group consisting of phosphoenolpyruvate carboxylase, aspartate aminotransferase, and aspartate semialdehyde dehydrogenase is further introduced or enhanced.

5. The microorganism of *Escherichia* sp. according to claim 1, wherein the microorganism is *Escherichia coli*.

6. A method for producing O-acetyl homoserine, comprising:
(a) culturing the microorganism of any of claims 1 to 3, 4 and 5; and
(b) recovering O-acetyl homoserine produced during the cultivation of the microorganism.

* * * * *